US012698921B2

(12) United States Patent
Lehman et al.

(10) Patent No.: US 12,698,921 B2
(45) Date of Patent: Aug. 4, 2026

(54) DUCT ADAPTOR FOR AN ION GENERATION DEVICE AND ION GENERATION DEVICE FOR USE THEREIN

(71) Applicant: Global Plasma Solutions, Inc., Charlotte, NC (US)

(72) Inventors: Joseph Lehman, Mooresville, NC (US); Jeremy Ferden, Salisbury, NC (US)

(73) Assignee: Global Plasma Solutions, Inc., Charlotte, NC (US)

( * ) Notice: Subject to any disclaimer, the term of this patent is extended or adjusted under 35 U.S.C. 154(b) by 649 days.

(21) Appl. No.: 17/897,418

(22) Filed: Aug. 29, 2022

(65) Prior Publication Data

US 2023/0069269 A1 Mar. 2, 2023

Related U.S. Application Data

(60) Provisional application No. 63/238,307, filed on Aug. 30, 2021, provisional application No. 63/238,323, (Continued)

(51) Int. Cl.
*F24F 13/02* (2006.01)
*A61L 9/22* (2006.01)
(Continued)

(52) U.S. Cl.
CPC ............ *F24F 13/0209* (2013.01); *A61L 9/22* (2013.01); *F24F 8/30* (2021.01); *H01T 23/00* (2013.01); *A61L 2209/15* (2013.01)

(58) Field of Classification Search
None
See application file for complete search history.

(56) References Cited

U.S. PATENT DOCUMENTS 1,811,687 A 6/1931 Philip et al.
3,624,448 A 11/1971 Saurenman
(Continued)

FOREIGN PATENT DOCUMENTS

AU 2014214642 A1 8/2015
CA 2108790 A1 4/1995
(Continued)

OTHER PUBLICATIONS

English machine translation for WO-9425783-A1 (Year: 1994).*
(Continued)

*Primary Examiner* — David E Smith
*Assistant Examiner* — Alina Kaliszewski
(74) *Attorney, Agent, or Firm* — Seth L. Hudson; Maynard Nexsen PC

(57) ABSTRACT

An adaptor for engagement to an air duct. The adaptor includes a back portion with an aperture within the back portion, a bellow adjacent the back portion with an opening positioned in a corresponding relationship with the aperture of the back portion, a top portion adjacent the bellow and spaced-apart from the back portion. A ring member is rotationally engaged to the back portion and disposed within the aperture of the back portion and the opening of the bellow. The ring member receives an ion generation device configured to engaged the ring member and containing a cleaning device for periodically cleaning a pair of electrodes.

20 Claims, 11 Drawing Sheets

Related U.S. Application Data filed on Aug. 30, 2021, provisional application No. 63/238,020, filed on Aug. 27, 2021.

(51) Int. Cl.
  F24F 8/30 (2021.01)
  H01T 23/00 (2006.01)

(56) References Cited

U.S. PATENT DOCUMENTS

| | | | | |
|---|---|---|---|---|
| 3,652,897 A | 3/1972 | Iosue et al. | | |
| 3,769,695 A | 11/1973 | Price et al. | | |
| 3,968,405 A | 7/1976 | Testone | | |
| 4,031,599 A | 6/1977 | Testone | | |
| 4,117,326 A | 9/1978 | Askman | | |
| 4,123,093 A * | 10/1978 | Newland | F16L 37/008 | |
| | | | 285/424 | |
| D253,281 S | 10/1979 | Kim | | |
| 4,216,518 A | 8/1980 | Simons | | |
| 4,263,636 A | 4/1981 | Testone | | |
| 4,264,343 A | 4/1981 | Natarajan et al. | | |
| 4,284,420 A * | 8/1981 | Borysiak | B03C 3/08 | |
| | | | 96/51 | |
| D286,765 S | 11/1986 | Prouty et al. | | |
| 4,734,580 A | 3/1988 | Rodrigo et al. | | |
| 4,757,422 A | 7/1988 | Bossard et al. | | |
| 4,809,127 A | 2/1989 | Steinman et al. | | |
| 4,829,398 A | 5/1989 | Wilson | | |
| 5,034,651 A | 7/1991 | Domschat | | |
| 5,065,034 A | 11/1991 | Kawanami et al. | | |
| 5,080,403 A * | 1/1992 | Paoluccio | F24F 13/0218 | |
| | | | 285/229 | |
| 5,084,077 A | 1/1992 | Junker et al. | | |
| D332,942 S | 2/1993 | Julien | | |
| 5,314,212 A * | 5/1994 | Sanders | F24F 13/0263 | |
| | | | 285/204 | |
| D353,575 S | 12/1994 | Macomber | | |
| 5,464,754 A | 11/1995 | Dennis et al. | | |
| 5,492,557 A | 2/1996 | Vanella | | |
| 5,653,638 A | 8/1997 | Nagata | | |
| 5,737,176 A | 4/1998 | Muz | | |
| 5,741,352 A | 4/1998 | Ford et al. | | |
| 5,768,087 A | 6/1998 | Vernitskiy | | |
| 5,879,435 A | 3/1999 | Satyapal et al. | | |
| 5,921,592 A * | 7/1999 | Donnelly | F16L 37/091 | |
| | | | 285/239 | |
| 5,931,989 A | 8/1999 | Knutsson | | |
| 6,019,815 A | 2/2000 | Satyapal et al. | | |
| 6,118,645 A | 9/2000 | Partridge | | |
| D434,523 S | 11/2000 | Ford | | |
| 6,156,099 A | 12/2000 | Hironaka et al. | | |
| D443,587 S | 6/2001 | Sakasegawa | | |
| 6,252,756 B1 | 6/2001 | Richie, Jr. | | |
| 6,330,146 B1 | 12/2001 | Blitshteyn | | |
| 6,350,417 B1 | 2/2002 | Lau et al. | | |
| 6,417,581 B2 | 7/2002 | Hall | | |
| 6,464,754 B1 * | 10/2002 | Ford | B03C 3/76 | |
| | | | 96/25 | |
| 6,544,485 B1 | 4/2003 | Taylor | | |
| D476,298 S | 6/2003 | Lee | | |
| 6,576,046 B2 | 6/2003 | Pruette | | |
| 6,653,638 B2 | 11/2003 | Fujii | | |
| 6,680,033 B2 | 1/2004 | Ishii | | |
| 6,744,611 B2 | 6/2004 | Yang et al. | | |
| 6,744,617 B2 | 6/2004 | Fujii | | |
| 6,791,814 B2 | 9/2004 | Adachi et al. | | |
| 6,850,403 B1 | 2/2005 | Gefter et al. | | |
| 6,855,190 B1 | 2/2005 | Nikkhah | | |
| 6,902,392 B2 | 6/2005 | Johnson | | |
| D533,832 S | 12/2006 | Hock | | |
| 7,177,133 B2 | 2/2007 | Riskin | | |
| 7,222,888 B1 * | 5/2007 | Piety | F24F 13/0209 | |
| | | | 285/260 | |
| 7,244,289 B2 * | 7/2007 | Su | B03C 3/41 | |
| | | | 422/186.04 | |
| 7,256,979 B2 | 8/2007 | Sekoguchi et al. | | |
| 7,273,515 B2 | 9/2007 | Yuen | | |
| 7,408,759 B2 | 8/2008 | Gefter et al. | | |
| D587,198 S | 2/2009 | Nagasawa | | |
| 7,492,568 B2 | 2/2009 | Takayanagi | | |
| 7,497,898 B2 * | 3/2009 | Sato | B03C 3/383 | |
| | | | 313/238 | |
| 7,639,472 B2 | 12/2009 | Sekoguchi et al. | | |
| 7,690,694 B2 * | 4/2010 | Poder | F16L 37/133 | |
| | | | 285/308 | |
| 7,716,772 B2 | 5/2010 | Shih et al. | | |
| 7,739,771 B2 | 6/2010 | Powell, Jr. | | |
| 7,764,482 B2 | 7/2010 | Lee et al. | | |
| 7,824,477 B2 * | 11/2010 | Kang | B03C 3/82 | |
| | | | 96/88 | |
| 7,916,445 B2 | 3/2011 | Sekoguchi et al. | | |
| 7,940,509 B2 | 5/2011 | Orihara et al. | | |
| 7,948,733 B2 | 5/2011 | Hashimoto | | |
| 7,961,451 B2 | 6/2011 | Sekoguchi et al. | | |
| 7,969,707 B2 | 6/2011 | Riskin | | |
| 7,995,321 B2 | 8/2011 | Shimada | | |
| 8,043,573 B2 | 10/2011 | Parker et al. | | |
| 8,053,741 B2 | 11/2011 | Sekoguchi | | |
| 8,106,367 B2 | 1/2012 | Riskin | | |
| 8,134,821 B2 | 3/2012 | Fukai | | |
| 8,328,902 B2 | 12/2012 | Boyden et al. | | |
| 8,351,168 B2 | 1/2013 | Sicard | | |
| 8,425,658 B2 | 4/2013 | Lee | | |
| 8,554,924 B2 | 10/2013 | Holden et al. | | |
| 8,710,455 B2 | 4/2014 | Shiozawa | | |
| 8,710,456 B2 | 4/2014 | Klochkov | | |
| 8,724,286 B2 | 5/2014 | Uchida et al. | | |
| 8,873,215 B2 | 10/2014 | Waddell | | |
| 8,951,024 B2 | 2/2015 | Ishii et al. | | |
| 8,957,571 B2 | 2/2015 | Riskin | | |
| 9,293,895 B2 | 3/2016 | Pucciani et al. | | |
| D754,314 S | 4/2016 | Ellis et al. | | |
| 9,579,664 B2 | 2/2017 | Marra | | |
| 9,623,422 B2 | 4/2017 | Overdahl | | |
| 9,630,185 B1 | 4/2017 | Riskin | | |
| 9,630,186 B2 | 4/2017 | Back | | |
| 9,660,425 B1 | 5/2017 | Sunshine | | |
| 9,661,725 B2 | 5/2017 | Gefter et al. | | |
| 9,661,727 B2 | 5/2017 | Gefter et al. | | |
| 9,847,623 B2 | 12/2017 | Sunshine | | |
| 9,849,208 B2 | 12/2017 | Waddell | | |
| 9,859,090 B2 | 1/2018 | Gefter | | |
| 9,948,071 B2 | 4/2018 | Chen et al. | | |
| 9,985,421 B2 | 5/2018 | Sunshine | | |
| 10,020,180 B2 | 7/2018 | Waddell | | |
| 10,116,124 B2 | 10/2018 | Sung et al. | | |
| 10,153,623 B2 | 12/2018 | Sunshine | | |
| 10,258,922 B2 | 4/2019 | Hsieh | | |
| D848,945 S | 5/2019 | Lin | | |
| 10,297,984 B2 | 5/2019 | Sunshine | | |
| 10,322,205 B2 | 6/2019 | Waddell | | |
| 10,439,370 B2 | 10/2019 | Sunshine | | |
| 10,492,285 B2 | 11/2019 | Lee et al. | | |
| 10,566,769 B2 | 2/2020 | Waddell | | |
| 10,633,783 B1 | 4/2020 | Kelly | | |
| 10,695,455 B2 | 6/2020 | Waddell | | |
| 10,710,098 B2 | 7/2020 | Marra | | |
| 10,737,279 B2 | 8/2020 | Gefter et al. | | |
| 10,758,947 B2 | 9/2020 | Heymann et al. | | |
| 10,786,818 B2 | 9/2020 | Galbreath et al. | | |
| 10,980,909 B2 | 4/2021 | Okano et al. | | |
| 10,980,911 B2 | 4/2021 | Waddell | | |
| 11,283,245 B2 | 3/2022 | Waddell | | |
| 12,220,503 B1 * | 2/2025 | Sorenson | A61L 9/22 | |
| 2003/0072697 A1 | 4/2003 | Taylor | | |
| 2003/0147783 A1 | 8/2003 | Taylor | | |
| 2006/0193100 A1 | 8/2006 | Izaki et al. | | |
| 2007/0253860 A1 | 11/2007 | Schroder | | |
| 2008/0130190 A1 | 6/2008 | Shimada | | |
| 2008/0160904 A1 | 7/2008 | Yi et al. | | |
| 2009/0052108 A1 | 2/2009 | Innami | | |
| 2009/0211459 A1 | 8/2009 | Hu et al. | | |

(56) References Cited

U.S. PATENT DOCUMENTS

| | | | |
|---|---|---|---|
| 2010/0157503 A1 | 6/2010 | Saito et al. | |
| 2010/0172808 A1 | 7/2010 | Igarashi | |
| 2010/0175391 A1 | 7/2010 | Jee et al. | |
| 2012/0068082 A1 | 3/2012 | Noda | |
| 2012/0154973 A1 | 6/2012 | Vaynerman et al. | |
| 2014/0076162 A1 | 3/2014 | Waddell et al. | |
| 2014/0078639 A1 | 3/2014 | Waddell et al. | |
| 2014/0103793 A1 | 4/2014 | Nishida et al. | |
| 2014/0147333 A1 | 5/2014 | Morfill | |
| 2014/0233232 A1 | 8/2014 | Radermacher | |
| 2014/0338705 A1 * | 11/2014 | Vasquez | F24F 13/029 134/22.12 |
| 2015/0255961 A1 | 9/2015 | Chen et al. | |
| 2015/0336109 A1 * | 11/2015 | Gefter | B03C 3/41 95/2 |
| 2016/0084415 A1 * | 3/2016 | Kirkpatrick | G06F 16/972 285/365 |
| 2016/0167059 A1 | 6/2016 | Waddell | |
| 2016/0175852 A1 * | 6/2016 | Waddell | B01D 53/32 96/51 |
| 2017/0040149 A1 | 2/2017 | Waddell | |
| 2017/0232131 A1 | 8/2017 | Waddell | |
| 2017/0274113 A1 | 9/2017 | Takasahara et al. | |
| 2018/0040466 A1 | 2/2018 | Waddell | |
| 2018/0071426 A1 | 3/2018 | Waddell | |
| 2018/0169711 A1 | 6/2018 | Waddell | |
| 2019/0247893 A1 | 8/2019 | Waddell | |
| 2019/0353359 A1 | 11/2019 | Seibold | |
| 2020/0161839 A1 | 5/2020 | Waddell | |
| 2020/0269263 A1 * | 8/2020 | Kikuchi | B05B 5/057 |
| 2020/0388994 A1 | 12/2020 | Waddell | |

FOREIGN PATENT DOCUMENTS

| | | | | |
|---|---|---|---|---|
| EP | 0919287 A2 | 6/1999 | | |
| EP | 1878506 A2 | 1/2008 | | |
| EP | 2336665 A1 | 6/2011 | | |
| EP | 2683042 A2 | 1/2014 | | |
| EP | 2411058 B1 | 5/2015 | | |
| EP | 2905036 A1 | 8/2015 | | |
| EP | 3093564 A1 | 11/2016 | | |
| EP | 3165833 A1 | 5/2017 | | |
| EP | 3346560 A1 | 7/2018 | | |
| GB | 1356211 A | 6/1974 | | |
| GB | 2117676 A | 10/1983 | | |
| GB | 2245200 A | 1/1992 | | |
| GB | 2301179 A | 11/1996 | | |
| GB | 2377660 A | 1/2003 | | |
| GB | 2415774 A | 1/2006 | | |
| GB | 2525280 A | 10/2015 | | |
| GB | 2529173 A | 2/2016 | | |
| KR | 100776572 B1 * | 11/2007 | | A61L 9/22 |
| KR | 20160138931 A * | 12/2016 | | H10P 70/20 |
| KR | 102100056 B1 | 4/2020 | | |
| WO | WO-8700089 A1 | 1/1987 | | |
| WO | WO-9425783 A1 * | 11/1994 | | E04F 17/04 |
| WO | WO-9820288 A1 | 5/1998 | | |
| WO | 2006039147 A2 | 4/2006 | | |
| WO | 2007009336 A1 | 1/2007 | | |
| WO | WO-2007131981 A1 | 11/2007 | | |
| WO | WO-2010014654 A1 | 2/2010 | | |
| WO | 2010074654 A1 | 7/2010 | | |
| WO | 2011136735 A1 | 11/2011 | | |
| WO | WO-2012176099 A1 | 12/2012 | | |
| WO | WO-2013173528 A1 | 11/2013 | | |
| WO | 2014047445 A1 | 3/2014 | | |
| WO | WO-2015111853 A1 | 7/2015 | | |
| WO | 2015138802 A1 | 9/2015 | | |
| WO | WO-2016082730 A1 | 6/2016 | | |
| WO | 2016134204 A1 | 8/2016 | | |
| WO | 2016204688 A1 | 12/2016 | | |
| WO | 2017155458 A1 | 9/2017 | | |
| WO | WO-2018175828 A1 * | 9/2018 | | H05F 3/06 |
| WO | 2018234633 A1 | 12/2018 | | |
| WO | 2019108898 A1 | 6/2019 | | |
| WO | WO-2021074280 A1 * | 4/2021 | | F24F 13/0209 |

OTHER PUBLICATIONS

English machine translation for KR-100776572-B1 (Year: 2007).*

English machine translation for WO-2021074280-A1 (Year: 2021).*

English machine translation for KR-20160138931-A (Year: 2016).*

Airmaid by Interzon product brochure; Sep. 2016; Interzon AB, Propellervagen 4A, SE-183 62 Taby, Sweden www.airmaid.com. 2 pages.

Extended European Search Report mailed on Sep. 28, 2021, in European Application No. 19750315.4, 60 pages.

Global Plasma Solutions. Link: https://gpshvac.com/wp-content/uploads/2017/07/GPS-FC48-AC-IOM-Rev.pdf Visited Jul. 5, 2019. GPS-FC48-AC-IOM-Rev Self-Cleaning Ion Generator Device. (Year: 2019) 2 pages.

"Products" Web Page, http://www.gpshvac.com/index.php?option=com_content&view=article&id=11&itemid=93, 1 Page, Apr. 29, 2013, retrieved from Internet Archive Wayback Machine, https://web.archive.org/web/20130429232411/ http://www.gpshvac.com/index.php?option=com_content&view=article&id=11&1temid=93 on Jan. 20, 2017.

"RGF Environmental Air Purification Technologies—Guardian Air HVAC Cell" Web Page, http://www.airstarsolutions.com/Pages/RGFguardian.aspx, 3 pages, Aug. 20, 2012, retrieved from Internet Archive Wayback Machine, https://web.archive.org/web/20120820000149/http://www.airstarsolutions.com/Pages/RGFguardian.aspx on Jan. 20, 2017.

Pushpawala Buddhi, et al., "Efficiency of Ionizers in Removing Airborne Particles in Indoor Environments." Journal of Electrostatics, vol. 90, pp. 79-84, Dec. 2017.

Wang, Wei, et al., "Assessment of Indoor Air Quality Using Different Air-Condition for Cooling." Advanced Materials Research, vol. 518-523, pp. 910-913, May 2012.

Wang, Yun Han, et al., "Research Progress of Air Purifier Principles and Material Technologies." Advanced Materials Research, vol. 1092-1093, pp. 1025-1028, Mar. 2015.

K. Nishikawa and H. Nojima, "Air purification technology by means of cluster ions generated by discharge plasma at atmospheric pressure." The 30th International Conference on Plasma Science, 2003. ICOPS 2003. IEEE Conference Record—Abstracts, pp. 379-, 2003.

* cited by examiner

DUCT ADAPTOR FOR AN ION GENERATION DEVICE AND ION GENERATION DEVICE FOR USE THEREIN

CROSS REFERENCE TO RELATED PATENT APPLICATION

The present patent application/patent claims the benefit of priority of U.S. Provisional Patent Application No. 63/238,020, filed on Aug. 27, 2021, and entitled "A DUCT ADAPTOR FOR AN ION GENERATION DEVICE"; U.S. Provisional Patent Application No. 63/238,307, filed Aug. 30, 2021, and entitled "SELF-CLEANING DEVICE FOR PRODUCING IONS"; and U.S. Provisional Patent Application No. 63/238,323, filed on Aug. 30, 2021, and entitled "SELF-CLEANING DEVICE FOR PRODUCING IONS WITH SEPARATE CONTROL PORTION", the contents of these provisional patent applications re incorporated in full by reference herein.

FIELD OF THE INVENTION

The present invention relates generally to the field of air treatment, and more particularly to the treatment of air using ionization.

BACKGROUND OF THE INVENTION

Ionization has been studied for almost a century and air ionization products have been available in the market for decades. Bipolar ionization uses ions as antimicrobial agents. Ions are atoms or molecules that have gained or lost one or more electrons, so they are electrically charged. Ions form naturally in the environment from such energy sources as UV light, frictional charging by the wind, water droplet breakup (waterfalls, sea waves), electrical discharge from lightning, etc. Bipolar ionization (BPI) refers to technologies that use an artificial source of energy to produce both positively charged ions (cations) and negatively charged ions (anions). The ions are typically produced by applying voltage to electrodes to create an electric field; as the air passes through the electric field, some atoms or molecules in the air stream may lose or gain electrons and become ions. Different electrical arrangements give rise to different variants of bipolar ionization devices, e.g., corona discharge, dielectric barrier discharge, needlepoint bipolar ionization (NPBI®), etc. There are BPI devices that can be installed in an air handling unit and/or in a duct operably coupled thereto.

Air handling units and/or ducts typically come in varying shapes and sizes, and so installing BPI devices relies on tailoring BPI devices to a particular geometry of the air handling unit and/or the duct, such as, for example, rectangular ducts, round ducts, oval ducts, and/or the like, to ensure a proper fitting. Therefore, there is a need of developing a universal adapter configured to allow installation of BPI devices to air handling units and/or ducts having curved and flat surfaces.

BRIEF SUMMARY OF THE INVENTION

Consistent with a disclosed embodiment, a duct adaptor is provided. The duct adaptor includes a flexible connecting element configured to adapt to a surface of a duct, the flexible connecting element having a first and the second edge, the second edge defining a hole. Further, the duct adaptor includes a ring element, the ring element connected to the second edge of the flexible connecting element.

Consistent with another disclosed embodiment, a method of attaching an ion generation device towards a surface is provided. The method includes forming a hole in the surface through which at least one of the ends of the ion generation device may be passed through and securing an adapter over the surface. The adapter includes a flexible connecting element configured to adapt to a surface of a duct, the flexible connecting element having a first and the second edge, the second edge defining a hole. Further, the duct adaptor includes a ring element, the ring element connected to the second edge of the flexible connecting element. The method further includes inserting the ion generation device into the adapter and securing the ion generation device against an element of the adapter configured to secure in place the ion generation device.

BRIEF DESCRIPTION OF THE DRAWINGS

The present invention is illustrated and described herein with reference to the various drawings, in which like reference numbers denote like method steps and/or system components, respectively, and in which.

DETAILED DESCRIPTION OF THE INVENTION

Figure 1:
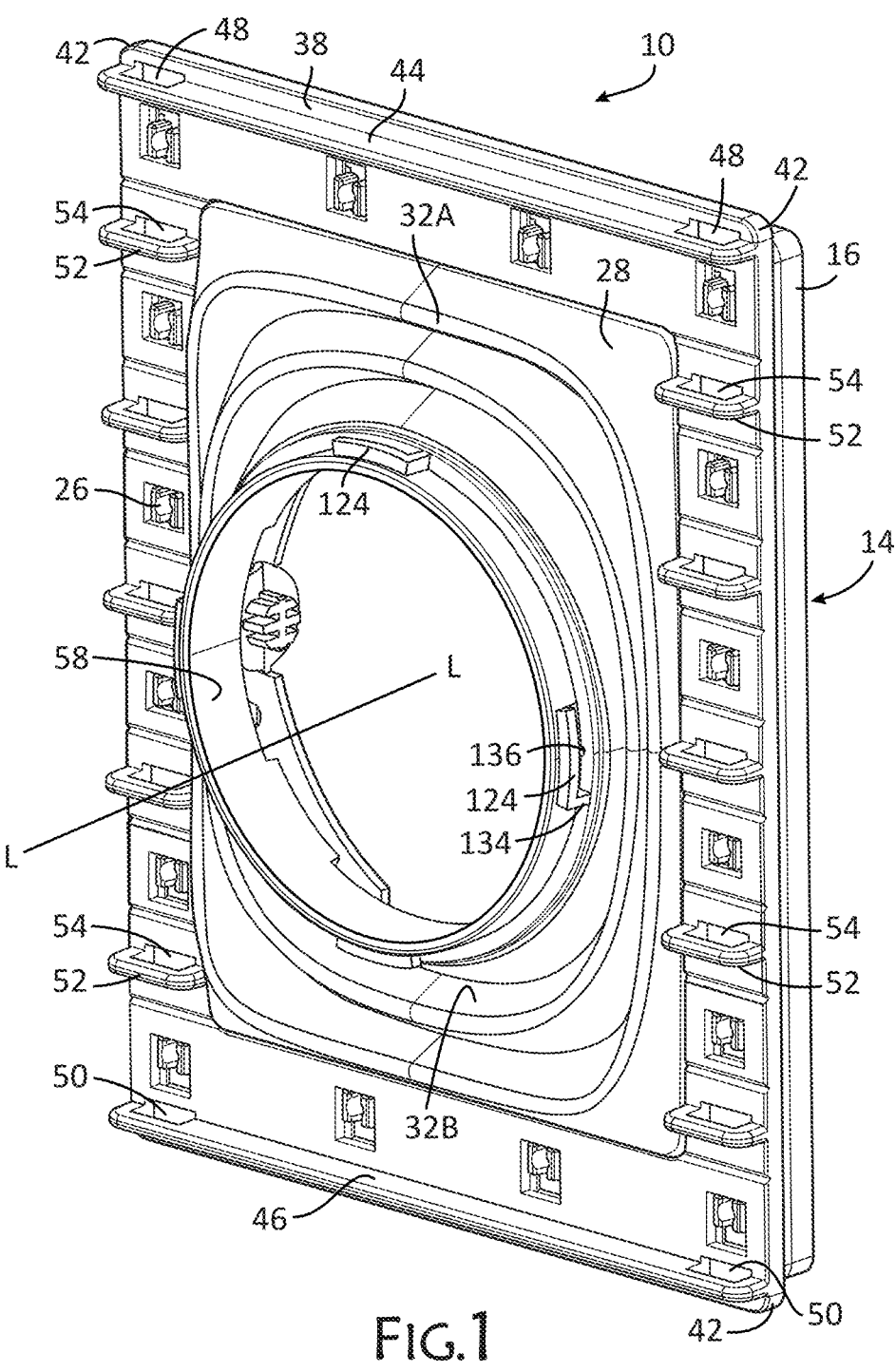
FIG. 1 is a perspective view of the adaptor.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Various embodiments described herein are related to ion generation devices used to ionize or otherwise treat air within an air-conditioning (HVAC) applications. One of the most widely used ionization approaches include bipolar ionization, which is commonly reported to reduce airborne particulate matter by causing them to cluster or agglomerate and form larger particles that can settle out of the air more rapidly or be filtered more effectively, neutralize odors and break down volatile organic compounds (VOCs), inactivate or kill viruses and other microorganisms, and reduce the amount of required outdoor air. Many engineers have been recommending bipolar ionization devices because of relatively low upfront costs for purchase and installation, low maintenance and materials costs, and they do not introduce additional pressure drop to air handling units.

An example ion generation device may include an ion generator and at least one pair of air ionizing electrodes (e.g., needlepoint electrodes for ion generation). In an example embodiment, needles for electrodes may include a stainless steel, carbon fiber, tungsten, steel or other conductive material (e.g. a suitable metal) are used and optionally further comprising onboard control circuitry. In an example embodiment, the ion generator produces approximately equal amounts of positive and negative ions, regardless of airflow velocity or other conditions such as humidity or temperature. In some cases, the ion generator may be configured to have suitable mechanisms for controlling the amount of negative or positive ions based on the environmental conditions (e.g., the amount of ions may be dependent on an air flow rate, a direction of the airflow, a temperature of the air, a humidity of the air, an amount of pollution expected or observed in the air, and the like). The amount of pollution in the air may be expected (e.g., based on a location, such as hospital, indoor dining place, and the like) or may be observed (e.g., via suitable sensors such as air transparency sensors, humidity sensors, sensors detecting presence of a person or a crowd of people, and the like). In example embodiment, each ion generator produces positive and negative ions in a concentration of at least about $10^9$ ions/second, and operates on 12V DC, 110V AC, or other power source. In alternate embodiments, the ion generator(s) generate negative ions only, or positive ions only, or generate negative and positive ions in unequal quantities. In example embodiments, the ion generator produces minimal or no ozone, for example at no greater concentration than in ambient air. Wiring may be routed through the housing for connection to an external power source, and a power inverter may be included to convert the source voltage to the required input voltage of the ion generator. Optionally, the ion generator automatically controls the ion discharge output based on preset algorithms, setpoints or other criteria, which may vary in relation to the airflow rate across the electrodes.

An example ion generator may include a power supply (or a power converter). In an example embodiment, the power converter may receive an alternative electrical power and convert it to a direct electrical power. Additionally, or alternatively, the power converter may be configured to modify the received voltage (including modification of amplitude and frequency of the received voltage). An ion generator may include a positive electrode and a negative electrode, with the power supply producing a potential difference between the positive and negative electrodes. In an example embodiment, both the positive and negative electrodes may be needlepoint electrodes. The positive and negative electrodes may have elongated linear shapes, elongated curved shapes circular shapes, square shapes, and the like. In some cases, the positive and negative electrodes may not be needlepoint electrodes, and other electrodes may be used (e.g., electrodes comprising meshes, carbon fibers, conductive fabric, and the like).

The present disclosure addresses an adaptor, positioning and securing an ion generation device using an adapter, and an ion generation device. In an example embodiment, an ion generation device is secured in place using the duct adapter. Some of the key functionalities of the duct adapter include hermetically closing a duct for which the duct adapter is used when the ion generation device is inserted into the adapter and securing the ion generation device within a conduit, such as an HVAC duct, such that the ion generation device is not affected (e.g., not moved, rotated, bended, and the like) by a flow of gases (air) within the conduit.

In some cases, a suitable adapter is configured to position the ion generation device within the conduit such that the electrodes of the ion generation device are aligned generally perpendicularly to the direction of the airflow across the ion generator. In some cases, the electrodes may be aligned along the direction of the airflow across the ion generator. In various embodiments, the electrodes of the ion generator are positioned in the airflow within the conduit to prevent recombination of the positively charged ions with the negatively charged ions. One or more ion generation devices can be installed within a conduit, such as an air duct, using an associated adapter as further discussed below.

Consistent with disclosed embodiments an adapter for installing an ion generation device and an ion generation device is provided. An example embodiment of an adapter 10 is shown in FIGS. 1-3, 4A, and 4B. Adapter 10 is configured to fit around a conduit, such as a duct 12. Duct 12 may include curved surfaces (e.g., duct 12 may have a circular cross-section and, as a result, may have a curved exterior surface). In various embodiments, adapter 10 is configured to adapt to various curved surfaces (e.g., concave surfaces, convex surfaces) as well as flat surfaces. In an example embodiment, in order to adapt to a curved surface, adapter 10 includes a flexible connecting element 14.

Figure 2:
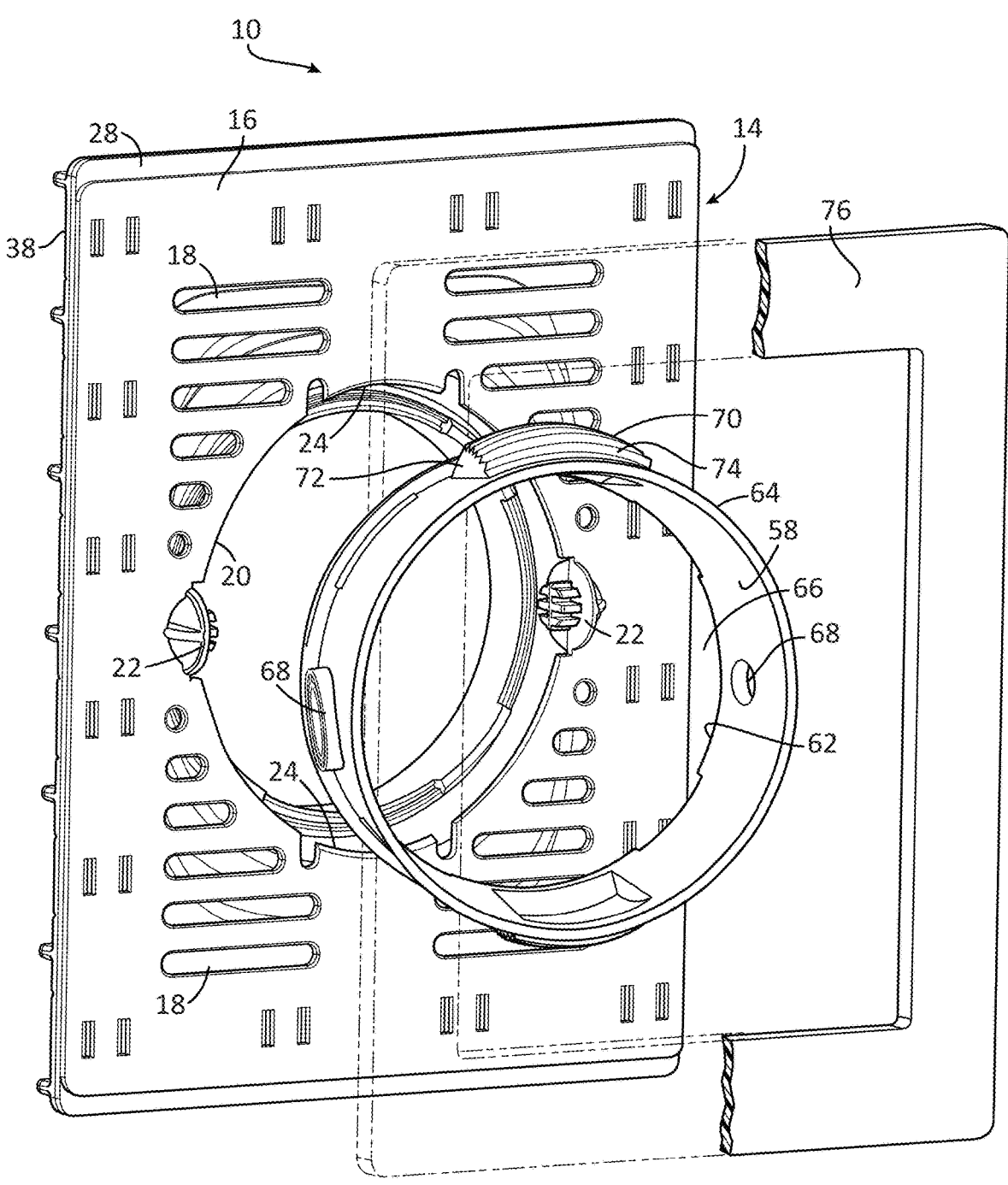
FIG. 2 is a partial exploded view of the adaptor.

The flexible connecting element 14 includes a back portion 16 that is flexible. The back portion 16 contains a plurality of slots 18, extending from the front side to the back side of the back portion 16. An aperture 20 is disposed within the back portion 16, extending from the front side to the back side of the back portion 16. The aperture 20 is an opening within the back portion 16 and may be generally circular as shown. The aperture 20 may be centrally located with the slots 18 spaced-apart and configured around the aperture 20 and preferably consisting of slot 18 with various sizes and dimensions. A pivot point 22 is disposed proximate the aperture 20, and preferably at least two pivot points 22 are disposed proximate the aperture 20. As illustrated in FIG. 2, two pivot points 22 are disposed proximate the aperture 20 and opposite each other. An adjustment engaging surface 24 is disposed on the periphery of the aperture 20. The adjustment engaging surface 24 may be tapered, preferably tapered from the front side to the back side and containing an edge proximate the aperture 20. The back portion 16 may contain two or more adjustment engaging surfaces 24 that are spaced-apart from each other, and as illustrated, two adjustment engaging surfaces 24 are disposed on the back portion 16 opposite each other and preferably configured on the periphery of the aperture 20. While the back portion 16 is illustrated as rectangular, the back portion 16 may have any geometric shape, such as circular, square, trapezoidal, and the like. A plurality of snap fittings 26 proximate the outer edge of the back portion 16 are configured to retain a bellow 28 within the flexible connecting element 14.

The bellow 28 is configured adjacent the front side of the back portion 16, containing an engaging surface 30, convolute sections 32a,32b, a ring member attachment portion 34, and an opening 36. The bellow 28 is flexible and contains convolute sections 32a,b, preferably configured between the engaging surface 30 and the opening 36, introducing a wide range of flexibility into the bellow 28. The convolute sections 32a,b are configured similar to pleats and behave like pleats, containing a ridge portion and a valley portion. Each ridge portion is separated by a valley portion, enabling the requisite flexibility for the bellow 28. The convolute sections 32a,b may be pulled apart from each other and brought towards each other in an expanded or contracted movement, enabling the bellow 28 to be capable of axial, lateral, or angular movement.

Figure 3:
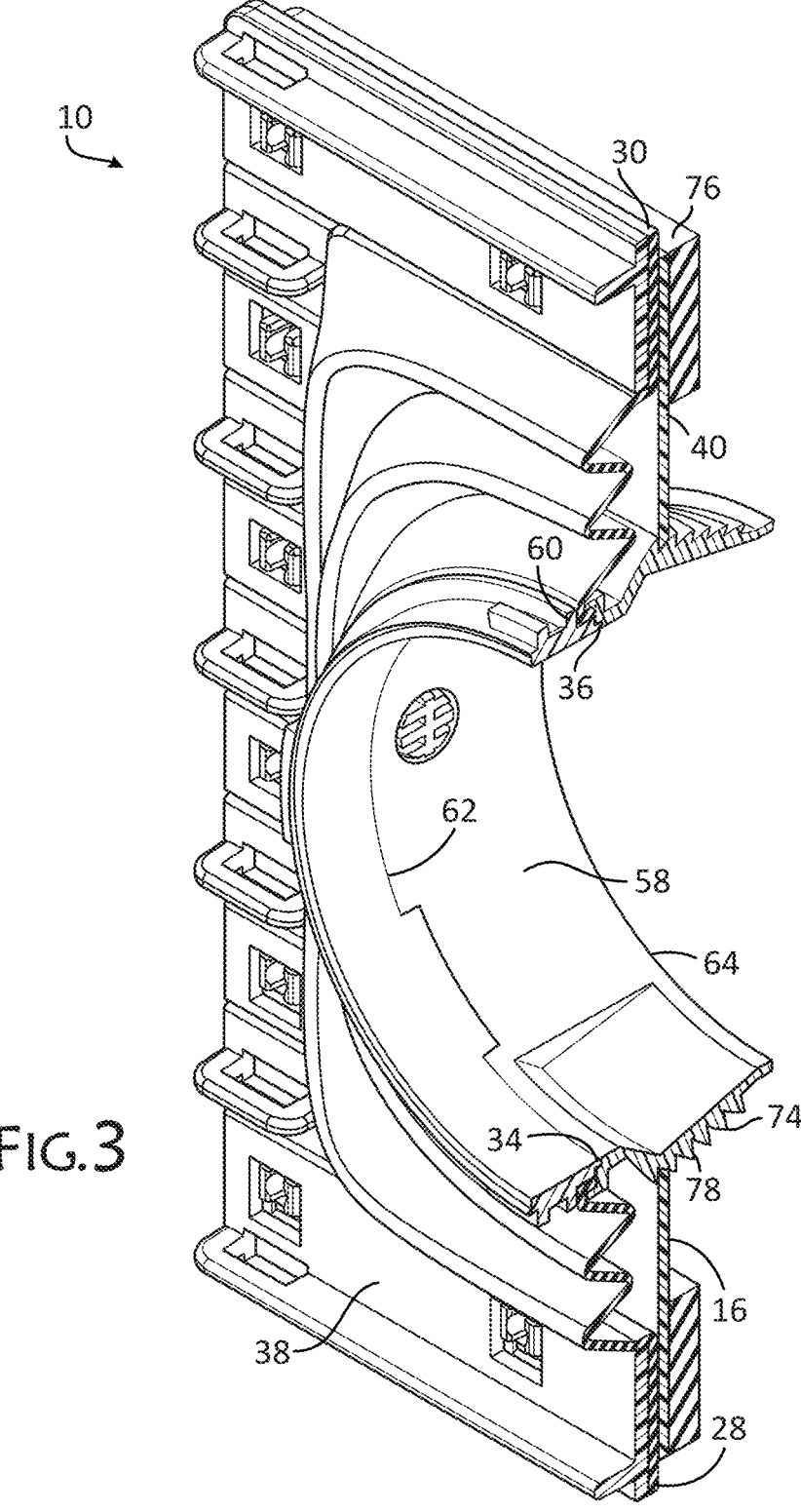
FIG. 3 is a partial cut-away view of the adaptor.

The opening 36 is disposed within the bellow 28 extending from the front surface to the back surface of the bellow 28. While the opening 36 may have any shape and location within the bellow 28, the opening, as illustrated in FIGS. 1 and 3, is centrally located within the bellow 28 and concentric. The ring member attachment portion 34 is adjacent the opening 36 of the bellow 28 and engages a ring member 58 received within the opening 36. The ring member attachment portion 34 is the portion of the bellow 28 that is engaged to the ring member 58. In some embodiments, the ring member attachment portion 34 may comprise a convolute sections 32a,b that is engaged to the ring member 38. While two convolute sections 32a,b are illustrated, the bellow 28 may have one convolute sections, two or more convolute sections, or a plurality of convolute sections. The bellow 28 may have any size, shape, or dimension, the bellow 28 as illustrated is rectangular, corresponding with the rectangular shape of the back portion 16. A portion of the back surface of the bellow 28 may be engaged to a portion of the front side of the back portion 16. Preferably, the periphery of the back surface of the bellow 28 is engaged to the periphery of the front side of the back portion 16. The periphery of the front side of the back portion 16 is preferably flat and smooth for engaging a correspondingly flat and smooth periphery of the back surface of the bellow 28. The periphery of the back surface of the bellow 28 is proximate the outer edge and proximate the convolute sections 32a,b. The periphery of the front side of the back portion 16 is proximate the outer edge and proximate the slots 18. The back surface of the bellow 28 may be engaged to the front side of the back portion 16 by snap fittings 26. Alternatively, or in addition to the snap fittings 26, the bellow 28 may be engaged to the back portion 16 by an adhesive or by a mechanical device, such as a screw, bolt/nut, rivet, and the like.

The back surface of the convolute sections 32a,b are disposed adjacent the slots 18 within the back portion 16. Preferably, the convolute sections 32a,b are disposed overtop or above the slots 18, when the bellow 28 is adjacent the back portion 16. The convolute sections 32a,b are not engaged to the slots 18 or the back portion 16. While the convolute sections 32a,b may contact the slots 18 or the back portion 16 depending upon the adjustment of the flexible connecting element 14 of the adaptor 10, the convolute sections 32a,b, are preferably spaced-apart from the slots 18.

A top portion 38 is adjacent to the engaging surface 30 of the bellow 28. As illustrated, the engaging surface 30 of the bellow 28 is disposed along the periphery of the bellow 28 proximate the outer edge and proximate the convolute sections 32a,b. The engaging surface 30 is preferably flat and smooth and configured for the correspondingly flat and smooth back surface or portions of the back surface of the top portion 38 to be placed adjacent the engaging surface 30. The top portion 38 is retained adjacent the bellow 28 by the snap fittings 26 extending from the back portion 16. A central opening 40 is disposed within the top portion 38, extending between the front surface to the back surface. While the central opening 40 may have any size, shape, dimension, or location within the top portion 38, as illustrated, the central opening 40 may have a rectangular shape and centrally located within the top portion 38. The convolute sections 32a,b are positioned within the central opening 40 and protrude through the central opening 40. The top portion 38 is configured around the convolute sections 32a,b, or in other words, the top portion 38 borders the convolute sections 32a,b, when the convolute sections 32a,b are positioned within the central opening 40. The bellow 28 may be made from any suitable airtight material (e.g., rubber, polymer, airtight fabric, a composite material comprising at least some of the sections being flexible, and/or stretchable, and the like).

The top portion 38 has a top side portion, a bottom side portion, and two opposed side portions. The two opposed side portions intersect the top side portion and the bottom side portion, defining corners 42. The corners 42 are preferably curved or rounded and without a sharp edge or point. An upper rib 44 extends along the front surface of the top side portion, and a lower rib 46 extends along the front surface of the bottom side portion. As illustrated, the upper rib 44 is proximate the outer edge of the top side portion, a first end is proximate one side edge and a second end is proximate the opposite side edge, and likewise, the lower rib 46 is proximate the outer edge of the bottom side portion, a first end is proximate one side edge and a second end is proximate the opposite side edge. An upper rib retention aperture 48 is configured proximate the first end of the upper rib 44 and another upper rib retention aperture 48 is configured proximate the second end of the upper rib 44. A lower rib retention aperture 50 is configured proximate the first end of the lower rib 46 and another lower rib retention aperture 50 is configured proximate the second end of the lower rib 46.

Figure 4A:
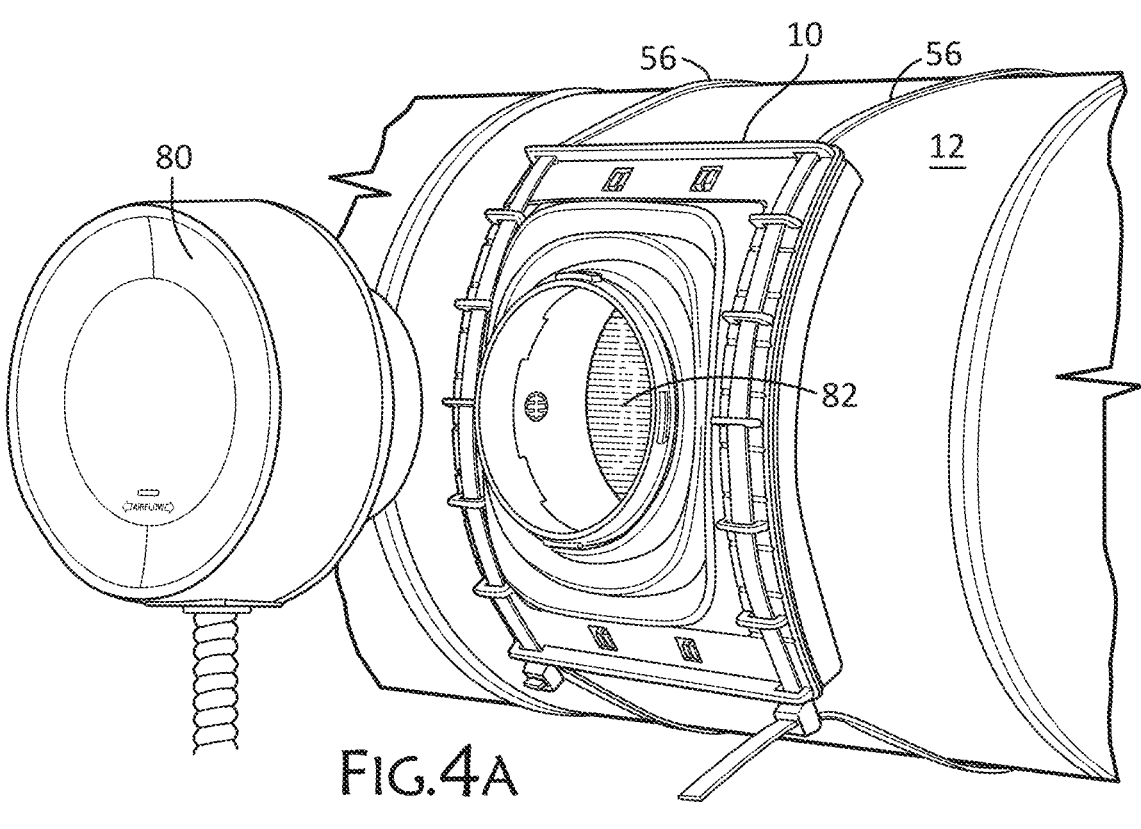
FIG. 4A is a perspective view of the adaptor engaged to a duct and the ion generation device.
Figure 4B:
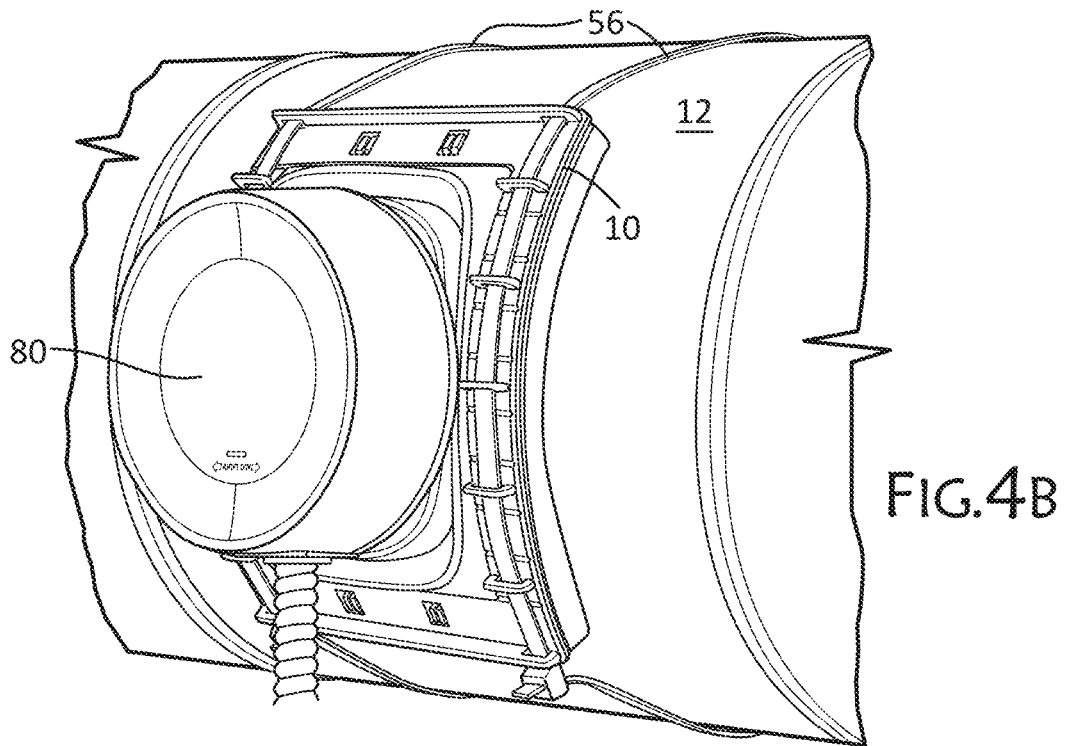
FIG. 4B is a perspective view of the adaptor engaged to a duct with the ion generation device engaged to the adaptor.

The two opposed side portions of the top portion 38 each contain at least one bracket 52. Preferably, the two opposed side portions of the top portion 38 each contain two or more brackets 52. More preferably and as illustrated, the two opposed side portions of the top portion 38 each contain a plurality of brackets 52. The brackets 52 are spaced-apart along the front surface of each side portion, and preferably spaced and equal distance apart along the front surface of each side portion. The placement of a bracket 52 or one side portion is aligned with a bracket 52 placed in an identical location on the other side portion. In other words, the brackets 52 may be placed in identical locations on each side portion. The brackets 52 each contain a bracket retention aperture 54 that extends through the bracket 52. The bracket 52 may have any shape, size, or dimension, but as illustrated, the bracket 52 has a reversed "u-shape" when viewing from the top of the adaptor 10, wherein the bracket retention aperture 54 is bounded on three sides by the bracket 52. The bracket retention apertures 54 on each side portion align when viewing from the top side or the bottom side of the adaptor 10. Additionally, the bracket retention apertures 54 on each side portion also align with the respective upper rim retention aperture 48 and lower rib retention aperture 50 for allowing an elongate retention device 56 to be received within each aperture 48, 50, and 54. The elongate retention device 56 may be a band clamp, cable tie, or zip tie. As illustrated in FIGS. 4A and 4B, an elongate retention device 56 is threaded through the brackets 52, the upper rib retention aperture 48, and the lower rib retention aperture 50 on one side of the top portion 38 and a second elongate retention device 56 is threaded through the brackets 52, the upper rib retention aperture 48, and the lower rib retention aperture 50 on the opposite side of the top portion 38. Both elongate retention devices 56 are wrapped around the exterior of the duct 12 and the ends of each elongate retention device 56 are engaged, securing or engaging the adaptor 10 to the duct 12.

The ring member 58 is configured to be engaged to the bellow 28. In one example embodiment, the ring member 58 is engaged to the ring element attachment portion 34 of the bellow 28 proximate the opening 36, allowing the ring member 58 to be received within the opening 36 and the bellow 28 engaged to the exterior surface of the ring member 58. The ring member 58 may have any shape, size, or dimension, but preferably the ring member 58 has a shape that corresponds with the opening 36. As illustrated, the opening 36 is circular and the ring member 58 has a circular cross-section. The ring member 58 may be configured with an exterior lip 60 on the exterior surface, serving as an engagement surface for engaging the ring member attachment portion 34 to the ring member 58. As illustrated, the lip 60 completely surrounds or circumscribes the exterior surface of the ring member 58.

The ring member 58 contains a first end 62 with an opening and a second end 64 with an opening and a passageway 66 extending between the opening in the first end 62 to the opening in the second end 64 along the longitudinal axis L-L. The ring member 58 is rotationally engaged to the back portion 16. A pivot point 68 is engaged to the ring member 58, and preferably two pivot points 68 are engaged opposite each other on the exterior surface of the ring member 58 that are rotationally engaged to the pivot point 22 of the back portion 16. The rotational engagement of the pivot points (22, 68) allows the ring member 58 to rotate within the aperture 20 of the back portion 16.

A ratchet member 70 is configured externally of the ring member 58. The ratchet member 70 consists of a base portion 72 and two or more spaced-apart ratchet ribs 74 oriented perpendicular to the longitudinal axis of the ring member 58. The ratchet ribs 74 are disposed within the base portion 72 and configured to receive the adjustment engaging surface 24 of the back portion 16. The base portion 72 is preferably angled in the longitudinal direction along the longitudinal axis L-L of the ring member 58. As illustrated, the base portion 72 is angled upwards along the longitudinal axis L-L of the ring member 58, wherein the height of the base portion 72 increases along the longitudinal axis L-L with the increase in height occurring in the direction from the second end 64 to the first end 62. The base portion 72 may be curved and contain a radius of curvature identical or similar to the radius of curvature of the ring member 58, when the ring member 58 has a circular cross-section as illustrated. As a result, the ratchet ribs 74 are also curved and have a radius of curvature identical or similar to the radius of curvature of the ring member 58, when the ring member 58 has a circular cross-section. Between each ratchet rib 74 is a trough 78 configured to receive the adjustment engaging surface 24 of the back portion 16. While the ring member 58 is rotationally engaged to the back portion 16, allowing the ring member 58 to rotate within the aperture 20 of the back portion 16, the adjustment engaging surface 24 in conjunction with the ratchet ribs 74 prevent the rotational movement of the ring member 58 within the aperture 20 when the adjustment engaging surface 24 is inserted into the trough 78 between each ratchet rib 74. Between the plurality of ratchet ribs 74 exist a plurality of troughs 78. The troughs 78 are formed between adjacent ratchet ribs 74. The adjustment engaging surface 24 is inserted into a desired trough 78 between adjacent ratchet ribs 74 for adjusting the position of the ring member 58 within the aperture 20 and retaining the ring member 58

At least one retention rib 124 may be disposed on the exterior surface of the ring member 58. They retention rib 124 assists with the engagement of an ion generation device 80 to the adaptor 10 and explained in more detail below.

The adaptor 10 may be attached to a conduit, such as a duct 12, as illustrated in FIGS. 4A and 4B. An optional padded portion 76 may be engaged to the back side of the back portion 16. The padded portion 76 may be composed of rubber or a foamed rubber or other like material that has a certain level of compression that assists with mounting the adaptor 10 to the duct 12. When the padded portion 76 is utilized with the adaptor 10, the padded portion 76 is placed on the surface of the duct 12. Preferably, an opening is cut-into a duct 12 that has a size similar, but slightly larger than the size of the ring member 58 that will be partially inserted into the opening 82 within the duct 12. The opening cut into the duct 12 is circular for receiving a ring member 58 that has a circular cross-section. The circular opening has a diameter slightly larger than the diameter of the ring member 58, allowing a portion of the ring member 58 to be partially inserted into the opening.

An ion generation device 80 suitable for engagement with the adaptor 10 is illustrated in FIGS. 4A, 4B, 5-9, and 13. The ion generation device 80 contains a base portion 84 with a bottom portion that extends to an outer edge and a sidewall extending upwardly from the outer edge to an upper edge. The bottom portion and the sidewall collectively form a cavity 86 therein. The base portion 84 contains an interior surface and an exterior surface. A substantially u-shaped slot 88 is disposed within the sidewall of the base portion 84 that extends from the upper edge of the sidewall towards the bottom portion, but preferably does not extend the entire sidewall, but has an end proximate the bottom portion. As illustrated, the base portion 84 generally has a circular cross-section.

An engagement member 90 is disposed within the cavity 86 of the base portion 84. The engagement member 90 contains at least one and preferably two or more elongate retention bores 92 that correspond with bores disposed on the interior surface of the base portion 84, preferably the bottom portion, for receiving an attachment device, such as a screw, bolt, or rivet for engaging the engagement member 90 to the base portion 84. An outwardly extending clip 94 extends from the engagement member 90. The outwardly extending clip 94 extends downwardly from the outer ring of the engagement member 90 and contains an aperture 96 within the clip 94. The clip 94 is configured to be received within the slot 88 of the base portion 84 and has a similar u-shape.

A top portion 98 is positioned on the engagement member 90. The top portion 98 contains a circular cross-section with a hollow interior for also housing some of the electrical components of the ion generation device 80. The top portion 98 contains a sidewall and an upper portion. A cleaning bar bore 100 and at least two electrode bores 102 are disposed within the upper portion of the top portion 98, extending from the exterior surface to the interior surface and providing access to the hollow interior of the top portion 98.

The top portion of the engagement member 90 contains an annular ring 152 disposed on the top portion of the engagement member 90. Some of the electrical components of the ion generation device 80 are positioned on the top portion of the engagement member 90 and inside the annular ring 152. The bottom edge of the top portion 98 may contain a lip extending outwards axially from the top portion 98. The outer edge and lip are positioned within the annular ring 152 and adjacent to the top portion of the engagement member 90. An o-ring may be positioned between the interior surface of the annular ring 152 and the top portion 98. The top portion 98 may contain at least one and preferably two or more retention bores that correspond with bores disposed on the engagement member 90 for receiving an attachment device, such as a screw, bolt, or rivet for engaging the top portion 98 to the engagement member 90.

A motor 104 is disposed within the hollow interior of the top portion 98. The motor 104 contains an elongate rotational shaft that rotates when the motor 104 is in the "on" position, or when the motor 104 is operating. The motor 104 receives power from a control printed circuit board. The rotational shaft is engaged to a cleaning device 106. The rotational shaft of the motor 104 is received within a downwardly extending hollow receptacle of the cleaning device 106. The receptacle may have a geometrically shaped cross-section that corresponds with a geometrically shaped cross-section of the rotational shaft forming a mating arrangement when the rotational shaft is received within the receptacle. For example, the cross-section of the receptacle may be "D-shaped" and the cross-section of the rotational shaft is correspondingly "D-shaped", allowing the rotational shaft to be received within the receptacle, forming a mating arrangement by the corresponding geometric shapes. As the rotational shaft of the motor 104 rotates, the cleaning device 106 also rotates.

The cleaning device 106 is preferably "t-shaped," meaning the receptacle is engaged to a top portion, wherein the top portion extends outwardly in two directions from the intersection where the receptacle is engaged to the top portion. The receptacle is engaged to the bottom surface of the top portion and extends outwardly from the bottom surface of the top portion of the cleaning device 106. The receptacle may extend through the cleaning bore 100 within the top portion 98 of the ion generation device 80 so the cleaning device 106 is configured to have the receptacle extending through the cleaning bore 100 and the top portion of the cleaning device 106 proximate the exterior surface of the upper portion of the top portion 98. The receptacle is matingly engaged to the shaft of the motor 104 within the top portion, allowing the receptacle and cleaning device 106 to rotate when the rotational shaft of the motor 104 rotates.

A motor vibration isolator and a gear vibration mount may also be utilized. Both the motor vibration isolator and the gear vibration mount are disposed around components of the motor 104. The motor vibration isolator is disposed on the bottom portion of the motor 104 to dampen or isolate any vibration caused by the operation of the motor 104. The gear vibration mount is disposed on the top portion of the motor

104 and covering a portion of the rotational shaft to dampen or isolate any vibration caused by the rotational spinning of the rotational shaft or any other forces exerted by the motor 104 during operation. The motor vibration isolator and the gear vibration mount are composed of a material such as rubber or plastic that has properties to dampen or isolate any vibration caused by the motor or rotational shaft.

The motor 104 is electrically coupled to a control module 108 for supplying power to operate the motor 104 and control the operation of the motor by turning the motor to the "on" position and the "off" position. The control module 108 may be positioned within the cavity 86 of the base portion 84 and proximate the bottom portion of the engagement member 90. The control module 108 contains a printed circuit board ("PCB") that carries a transformer, high voltage diodes, and the like. The control module 108 is engaged to an external power source for supplying the requisite power for the components of the ion generation device 80. Preferably, the wiring supplying the power to the control module 108 from the external power source is routed through the ion generation device 80 and preferably the aperture 20 in the back portion 16 and aperture 96 in the clip 94 for connection to the external power source. A conduit may be disposed within the aperture 96 of the clip 94 for routing the wiring from the control module 108 to the external power source. A power convertor may be included to convert the source voltage to the required input voltage of the ion generation device 80. A power convertor may also be contained within the device 10 to receive an alternating electrical power and connect it to a direct electrical power. The power converter may be contained on the PCB of the control module 108. Additionally, or alternatively, the power converter may be configured to modify the received voltage, including modification of amplitude and frequency of the received voltage. The control module 108 contains the logic for the cleaning cycle of the cleaning device 106 and also operates and drives the motor 104.

A first voltage wire 110 and a second voltage wire 112 are electrically coupled to an ionization module 160. The ionization module 160 contains a control printed circuit board ("PCB") and is electronically coupled to the control module 108. The ionization module 160 converts voltage from the control module 108 to a higher voltage for the generation of ions and ultimate emission of the ions from the upper end of the electrodes 114. The first voltage wire 110 and the second voltage wire 112 contain a first end and a second end. The first end is electrically coupled to the ionization module 160, and electrodes 114 that are air ionizing (e.g. needlepoint electrodes for emitting ions) are coupled to the second end of the first voltage wire 110 and the second voltage wire 112. The electrodes 114 may be composed of stainless steel, carbon fiber, tungsten, steel or other conductive material (e.g. suitable material). The electrodes 114 may consist of a plurality of carbon fibers extending outwardly from the second end of the first voltage wire 110 and a plurality of carbon fibers extending outwardly from the second voltage wire 112, as illustrated. In this embodiment, the electrodes 114, comprised of a plurality of carbon fibers, are coupled, for example by crimping, the electrode 114 to the second end of the first voltage wire 110 and the electrode 114 to the second end of the second voltage wire 112. In another embodiment, the electrode 114 is coupled to the second end of the first voltage wire 110 and the second voltage wire 112 by heat shrink. Current flows through the first voltage wire 110 and the second voltage wire 112, wherein the electrodes 114 emit ions from the upper end opposite the end engaged to the first voltage wire 110 and the second voltage wire 112 or at the distal end of the fibers and into the surrounding air. The ionization module 160 is preferably disposed within the hollow interior of the top portion 98 and may contact of be disposed proximate the top portion of the engagement member 90.

In one embodiment, the electrodes 114 are composed of a plurality of fibers composed of a thermoplastic polymer imbedded with conductive material that allows the polymer to conduct electricity. For example, the fibers may be composed of polypropylene or polyethylene and impregnated with carbon. Generally, the fibers may contain between about 20 to about 80 wt % polypropylene copolymer or polyethylene copolymer, between about 5 to about 40 wt % talc, and from about 5 to 40 wt % carbon black. However, any other resistive, inductive, reactive or conductive plastic or non-metallic material may be utilized for the fibers. The electrodes 114 may be replaceable and allowed to be easily disengage and new, unused electrodes 114 may be coupled to the first voltage wire 110 and the second voltage wire 112.

Figures 5, 6:
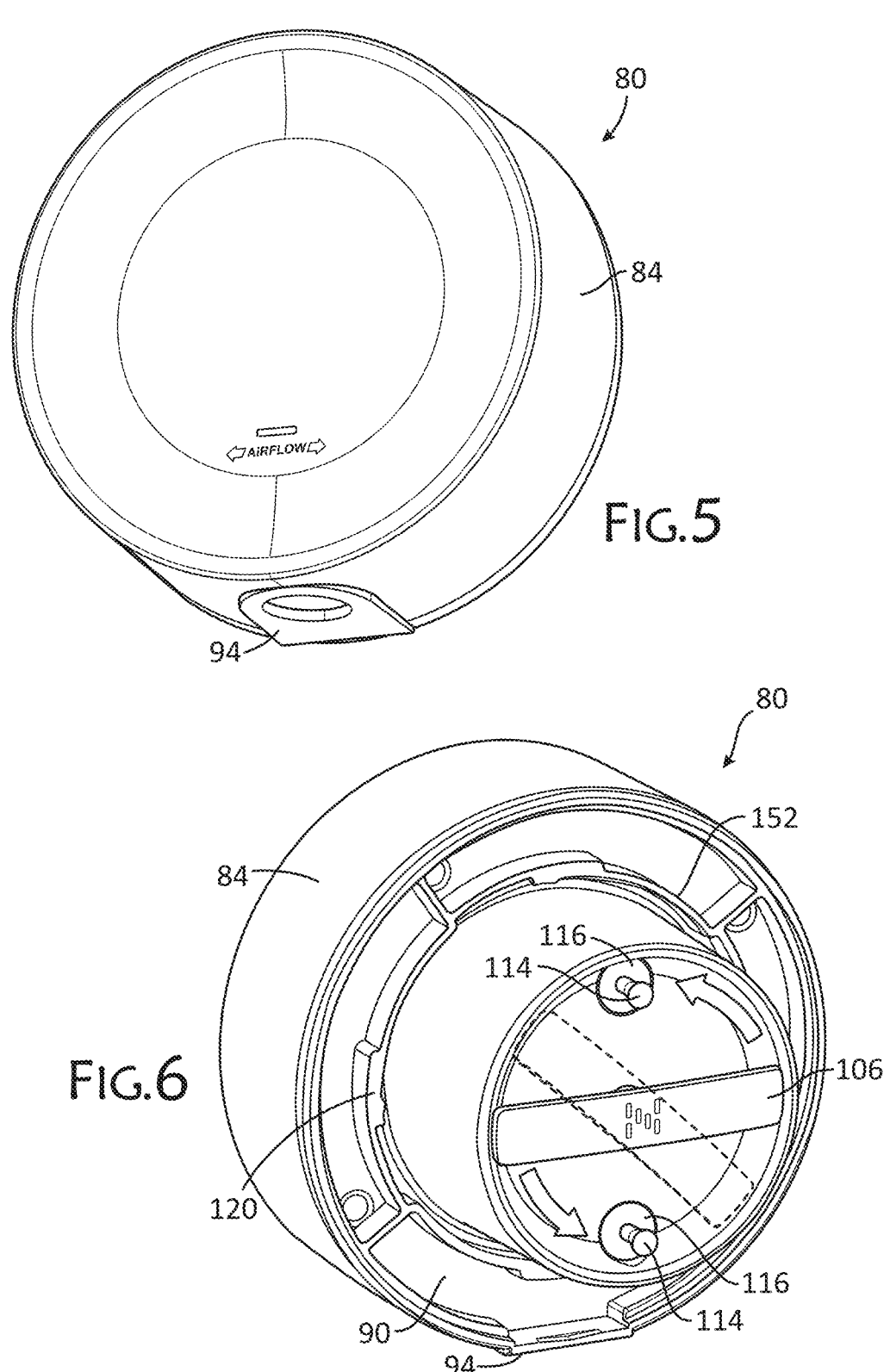
FIG. 5 is a front perspective view of the ion generation device.
FIG. 6 is a back perspective view of the ion generation device.
Figure 7:
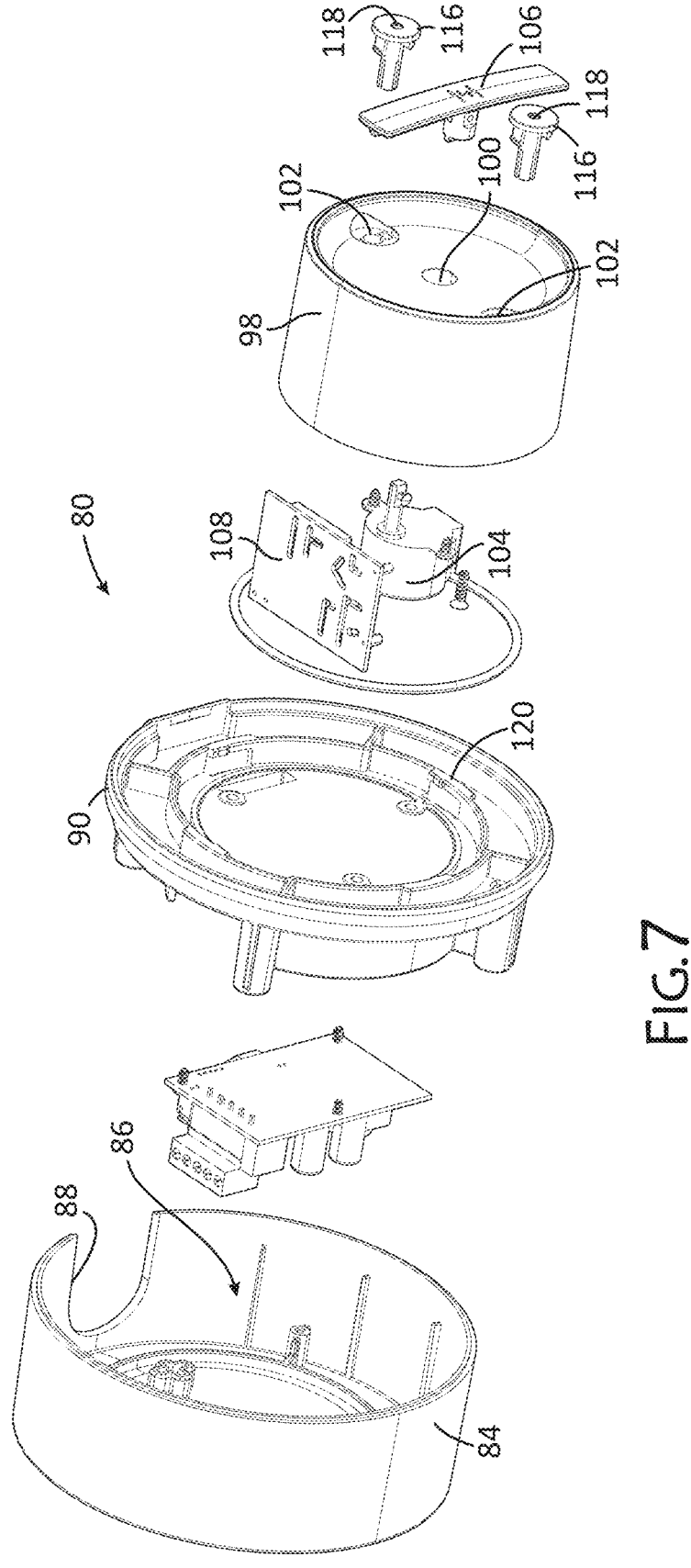
FIG. 7 is an exploded view of the ion generation device.
Figure 8:
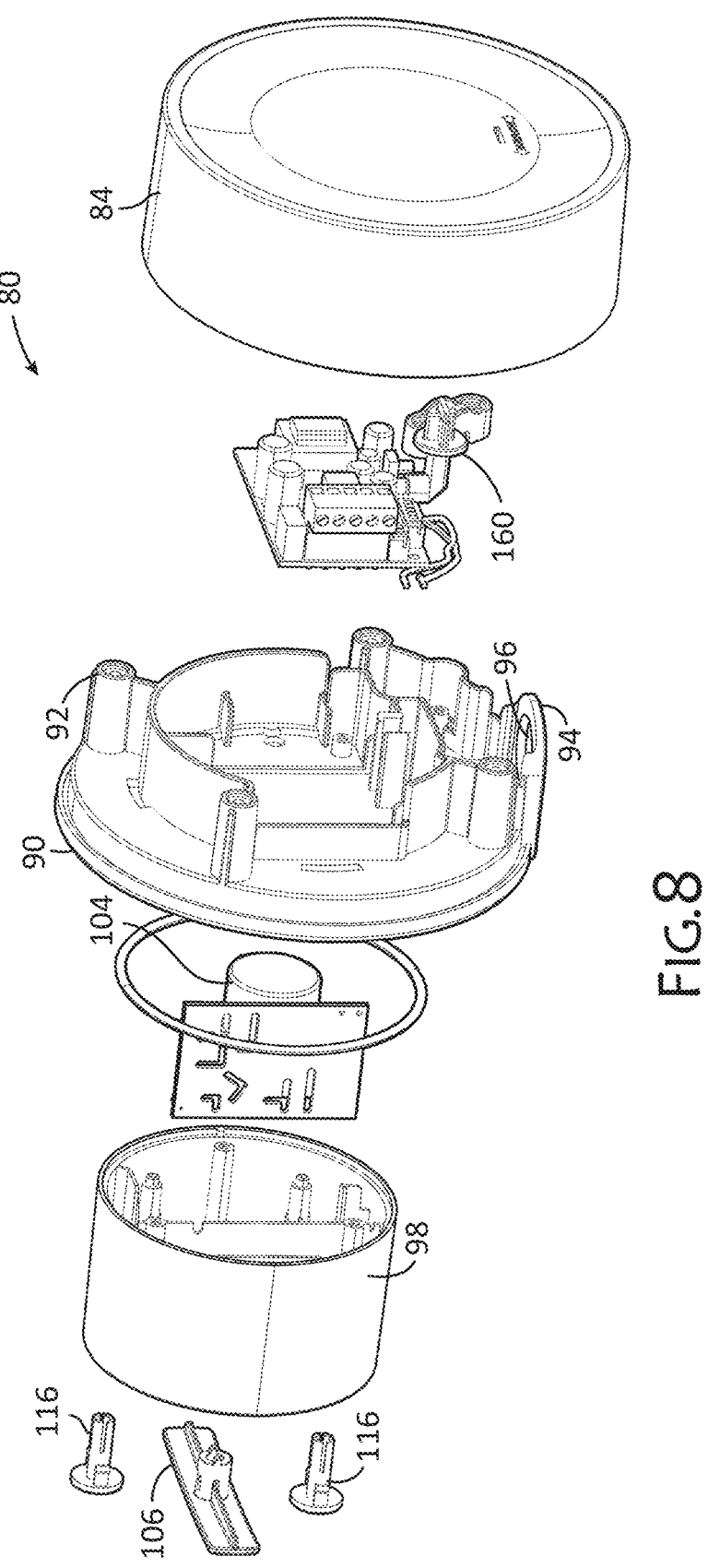
FIG. 8 is another exploded view of the ion generation device.
Figure 9:
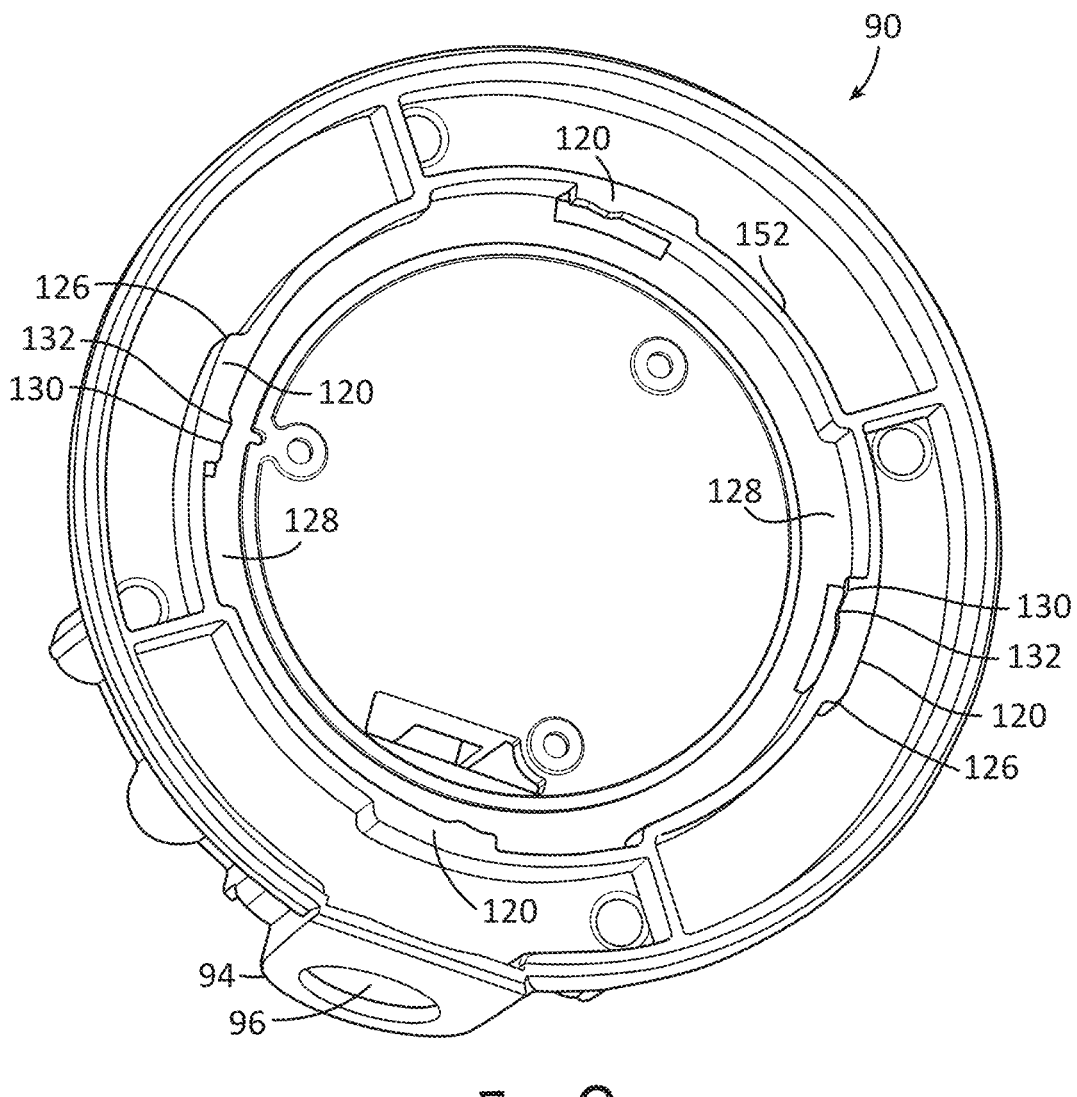
FIG. 9 is a perspective view of the engagement member.
Figures 10, 11:
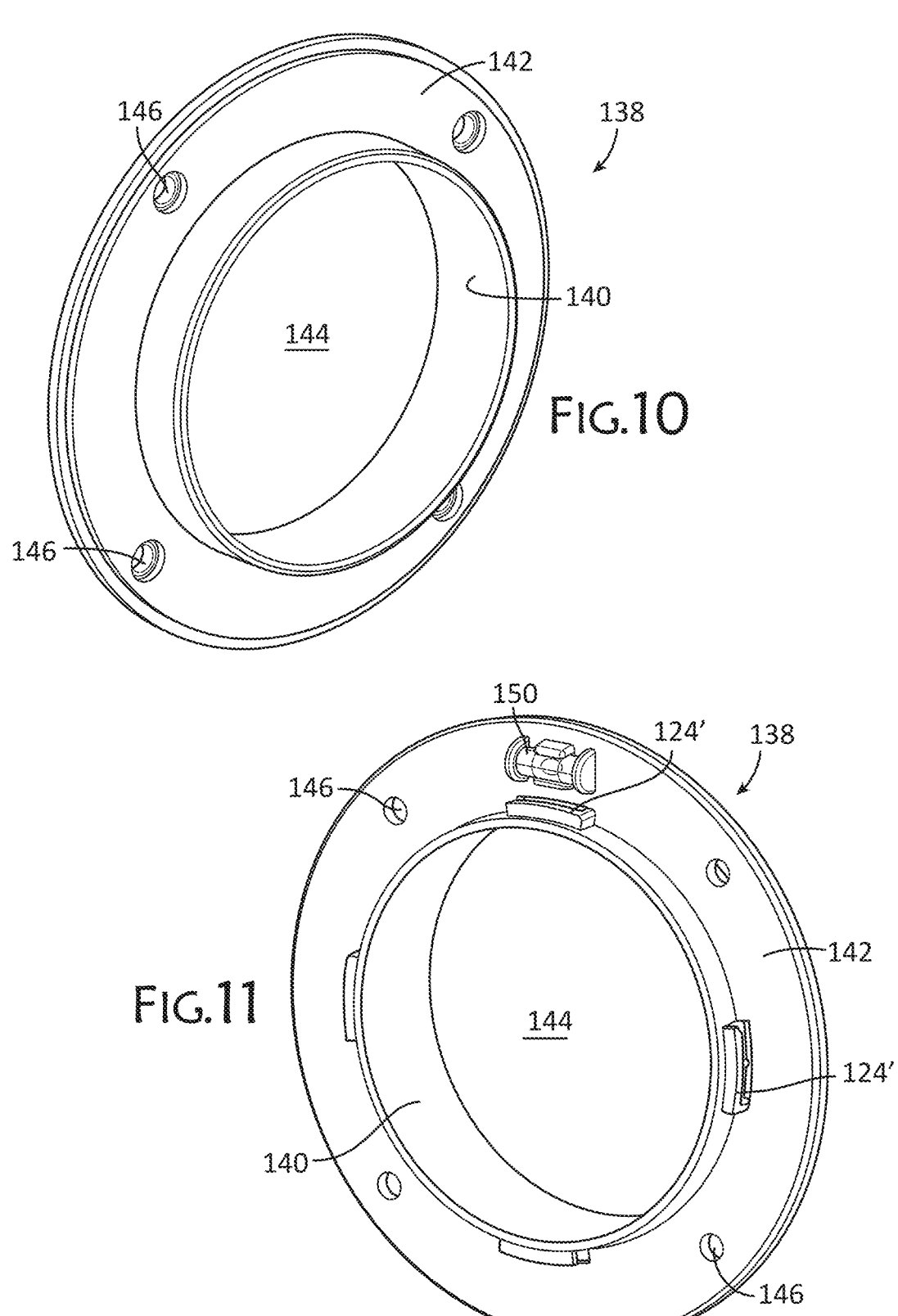
FIG. 10 is a back perspective view of the mounting ring.
FIG. 11 is a front perspective view of the mounting ring.
Figure 12:
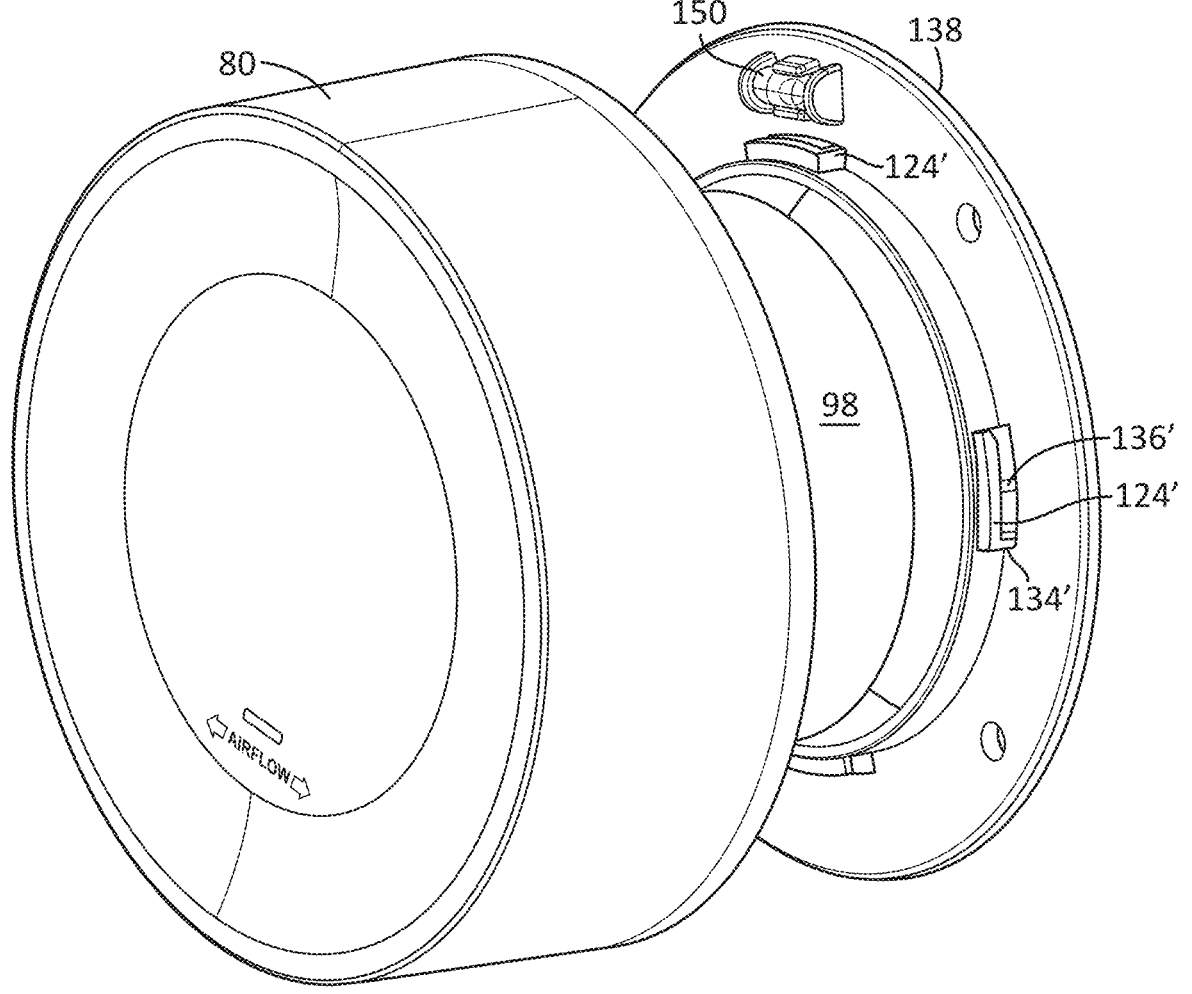
FIG. 12 is a perspective view of an ion generation device and the mounting ring.
Figure 13:
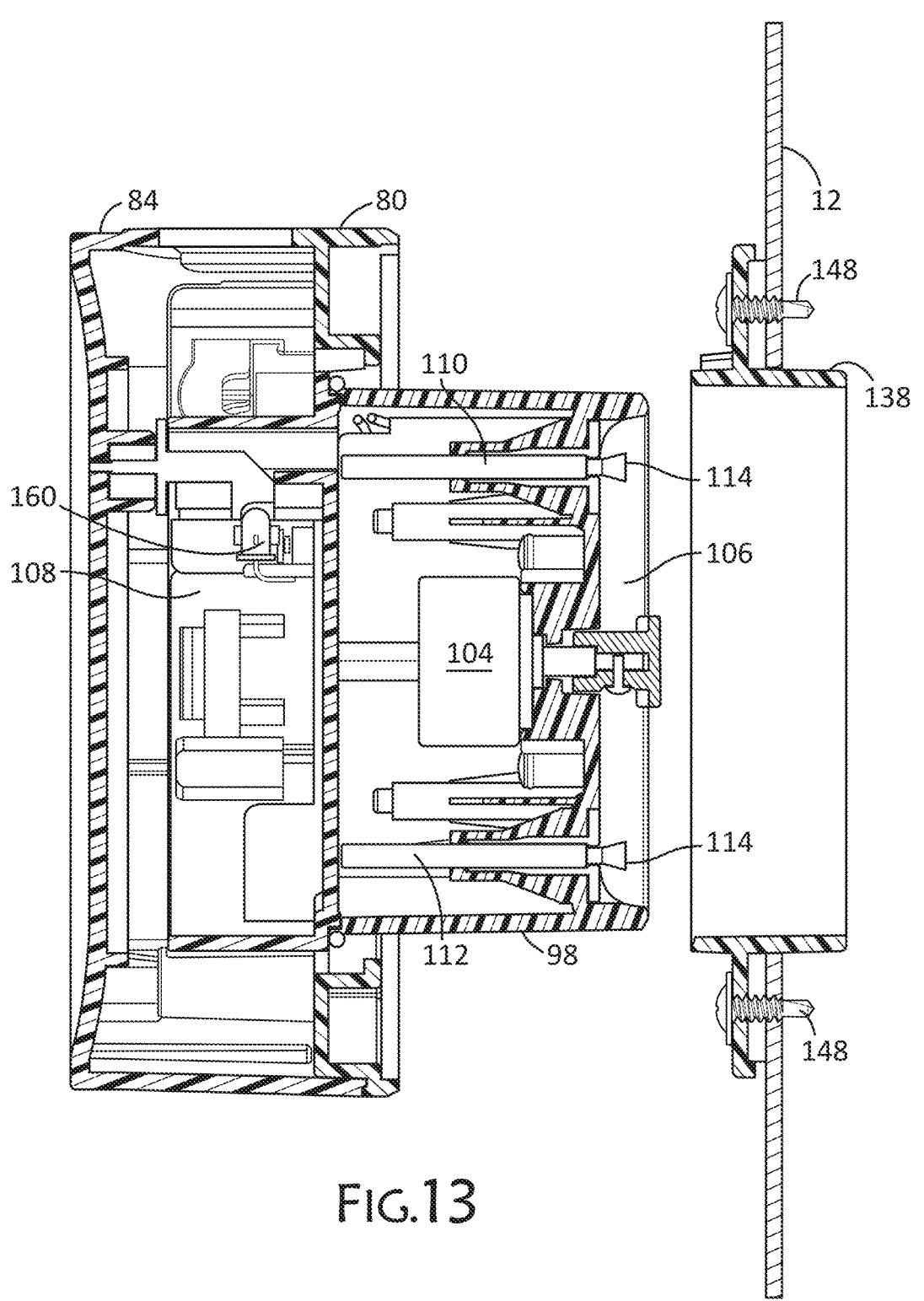
FIG. 13 is a cut-away side view of the ion generation device and mounting ring within a duct.

A separate electrode 114 extends through each electrode bore 102 on the top portion 98 of the ion generation device 80. Each electrode 114 extends from the hollow interior within the top portion 98 through each electrode bore 102, such that the upper end of the electrode 114 that emits ions is proximate the upper portion of the top portion 98. As illustrated in FIGS. 6-8, electrode retention clips 116 may be disposed within each electrode bore 102. The electrode retention clips 116 contain a circular top portion with a downwardly extending hollow shaft. A bore 118, preferably centrally located within the top portion, corresponds with the hollow interior portion of the shaft. Two resiliently flexible fingers extend from the bottom side of the top portion containing outwardly extending protrusions. The two resiliently flexible fingers are spaced-apart from each other and opposite each other with the hollow shaft there between. The resiliently flexible fingers contain a first end engaged to the bottom side of the top portion of the electrode retention clip 116 and extend outwardly to a second end. The second end contains a lip. Two slots are disposed within the upper portion of the top portion 98 on opposed sides of each electrode bore 102 and designed to receive the resiliently flexible fingers. The hollow shaft of the electrode retention clip 116 is received within the electrode bore 102 and each resiliently flexible finger is received within the slot on the upper portion of the top portion and for retaining the electrode retention clips 116 within the electrode bore 102 making a latching engagement with the top portion 98. The exterior surface of the upper portion of the top portion 98 may contain a recessed seating area within the upper portion that surrounds the electrode bore 102. The slots disposed on opposing sides of the electrode bore 102 may also be positioned within the recessed seating area. The circular top portion of the electrode retention clips 116 may be positioned within the recessed seating area, which may be correspondingly circular, when the hollow shaft is received within the electrode bore 102. As illustrated, the top side of the top portion is preferably flush with the exterior surface of upper portion of the top portion 98.

The first voltage wire 110 and the second voltage wire 112 may partially extend through the hollow interior portion of the shaft of the electrode retention clips 116. The electrodes 114 that are engaged to the second end of the first voltage wire 110 and the second voltage wire 112 may also partially extend through the hollow interior portion of the shaft of the electrode retention clips 116 and extend through the bore 118 within the top portion of the electrode retention clips 116 such that the upper end of the electrodes 114 are proximate to the exterior surface of the upper portion of the top portion 98. Alternatively, each of the electrodes 114 may extend through each hollow interior portion of the shaft of the electrode retention clips 116 and extend through the bore 118 within the top portion of the electrode retention clips 116, wherein the upper end of the electrodes 114 are positioned above the exterior surface of the upper portion of the top portion 98 and exposed to the air surrounding the ion generation device 80 for emitting ions into the air.

The top portion of the cleaning device 106, which is the portion of the cleaning device 106 that is perpendicular to the receptacle, contains a top surface and a bottom surface. The top surface is preferably smooth without any ribs, channels, or other protrusions. The bottom surface preferably contains two ribs extending from the intersection of the top portion and the hollow receptacle to opposed outer edges of the top portion. In other words, one rib extends from the intersection of the top portion and hollow receptacle to an outer edge, and the second rib extends in the opposite direction from the intersection of the top portion and hollow receptacle to the opposed outer edge of the cleaning device 106. In operation, while the cleaning device 106 is rotated by the motor 104, the first rib and the second rib contact the upper end of the electrodes 114 extending through the bore 118 of the electrode retention clips 116 to remove any dust, dirt, or other debris that may have accumulated on the electrodes 114 during operation.

The top portion 98 is preferably centrally located within the engagement member 90 and within the interior of the annular ring 152 bounded by the interior surface. The interior surface of the annular ring 152 contains at least one engagement strut 120 that projects radially inwardly from the annular ring 152. Preferably, the interior surface of the annular ring 152 contains two or more engagement struts 120 that project radially inwardly from the annular ring 152. More preferably and as illustrated, the interior surface of the annular ring 152 contains four engagement struts 120 spaced-apart around the interior surface of the annular ring 152, and preferably spaced an equal distance apart around the interior surface of the annular ring 152, that project radially inwardly from the annular ring 152. The engagement struts 120 are dimensioned and configured to facilitate rotational engagement of the ion generation device 80 within the ring member 58 of the adaptor 10. The engagement struts 120 are spaced apart from the exterior surface of the sidewall of the top portion 98 for allowing a portion of the ring member 58 of the adaptor 10 to be inserted into the space between the annular ring 152 and engagement struts 120 extending radially inwardly and the exterior surface of the sidewall of the top portion 98. Alternatively, the engagement struts 120 are dimensioned and configured to facilitate rotational engagement of the ion generation device 80 with a mounting ring 138. The passageway 66 of the ring member 58 is dimensioned and configured to receive the top portion 98 of the ion generation device 80 for positioning the electrodes 114 and cleaning device 106 within the duct 12 the adaptor 10 is engaged.

The interior surface of the ring member 58 serves as the outer boundary of the passageway 66. The exterior surface of the ring member 58 contains at least one retention rib 124, preferably two or more retention ribs 124, and more preferably four retention ribs 124, or any number of retention ribs 124 that correspond with the number of engagement struts 120 disposed on the ion generation device 80. The retention ribs 124 are spaced-apart around the exterior surface of the ring member 58, preferably spaced an equal distance apart around the exterior surface of the ring member 58, and project radially outwardly for frictionally engaging with the corresponding engagement strut 120. The retention ribs 124 are spaced from one another to allow the engagement struts 120 to fit there between when the top portion 98 of the ion generation device 80 is inserted within the passageway 66 of the ring member 58, during installation.

The engagement struts 120 are preferably partially annular and correspond with the shape of the annular ring 152 of the engagement member 90, which preferably has a circular cross-section. The engagement struts 120 have a shoulder portion 126 disposed adjacent a receiving area 128. The receiving area 128 is disposed between adjacent engagement struts 120 for receiving a retention rib 124 of the ring member 58 prior to engaging with the engagement strut 120. The receiving area 128 is bounded by two adjacent engagement struts 120, the interior surface of the annular ring 152, and the exterior surface of the top portion 98. The increase in width of the annular ring 152 between the receiving area 128 to the initial portion of the engagement strut 120 forms the shoulder portion 126. An engaging surface 130 is disposed proximate the shoulder portion 126, containing a cam surface 132 that is ramped. The cam surface 132 is defined by a portion of the engaging surface 130 extending radially inwardly from the annular ring 152, or in other words extending upwardly when progressing from the shoulder portion 126 along the engaging surface 130 of the engagement strut 120 and then proceeding radially outwardly, or in other words extending downwardly when progressing from the shoulder portion 126 along the engaging surface 130 of the engagement strut 120. The engaging surface 130 extends along the remainder of the engagement strut 120 and terminates proximate the adjacent receiving area 128.

The retention ribs 124 contain an upper surface and a bottom surface, the initial portion of the upper surface may be inclined to facilitate rotational engagement of the ion generation device 80 with the ring member 58 of the adaptor 10. While the initial portion of the upper surface of the retention rib 124 may be inclined, the remaining portion of the upper surface is generally flat or linear and configured to receive the engaging surface 130 of an engagement strut 120. The retention rib 124 may not have an inclined initial portion and maintain a generally constant width along the length of the retention rib 124. Stop surfaces 134 are disposed on the distal end of the retention rib 124 that limits rotational movement of the ion generation device 80 within the passageway 66 of the ring member 58. A tab 136 is disposed proximate the retention rib 124 and spaced-apart from the stop surface 134 of the retention rib 124 and perpendicular to the upper surface retention rib 124. The retention rib 124 is disposed between the lip 60 and an outer edge of the ring member 58 not covered or obstructed by the bellow 28. The tab 136 may extend between the lip 60 to the upper surface of the retention rib 124. Likewise, the stop surface 134 may extend between the lip 60 to the upper surface of the retention rib 124.

During engagement of the ion generation device 80 to the adaptor 10, the top portion 98 of the ion generation device 80 is received within the passageway 66 of the ring member 58 of the adaptor 10 until the outer edge of the ring member 58 contacts the engagement member 90 of the ion generation device 80. The ion generation device 80 is inserted into the passageway 66 so that the retention ribs 124 are initially received into the receiving area 128 proximate each engagement strut 120. The ion generation device 80 is rotated, preferably clockwise, causing the engaging surface 130 to contact the upper surface of the retention rib 124 and slide along the upper surface of the retention rib 124. As the engaging surface 130 proceeds along the upper surface of the retention rib 124, the engaging surface 130 also slides along the exterior surface of the tab 136 and the cam surface 132 slides along the upper surface of the retention rib 124 and exterior surface of the tab 136. Once the downside or declining portion of the cam surface 132 progresses past the tab 136, the tab 136 resists movement in the counter-clockwise direction because of a slight point or edge within on the cam surface 132 engages the tab 136 and the tab 136 prevents further movement in the counter-clockwise direction. As the ion generation device 10 is rotated, the shoulder portion 126 engages the top surface 134, preventing further movement in the clockwise direction of the ion generation device 80.

An optional mounting ring 138 is illustrated in FIGS. 10-13 that may be utilized instead of the adaptor 10 for mounting the ion generation device 80 to a duct 12 that has a generally flat, instead of curved, surface. The mounting ring 138 contains a longitudinally extending inner ring 140 and an annular flange 142 that extends radially outward from exterior surface of the inner ring 140. A passageway 144 is disposed within the mounting ring 138 and the inner surface of the inner ring 140 defines the boundary of the passageway 144. At least one mounting bore 146 is disposed within the flange 142, and as illustrated and preferred, a plurality of mounting bores 146 are disposed within the flange 142, extending from the interior surface to the exterior surface. The mounting bores 146 are configured to receive an engagement device 148 for mounting the mounting ring 138 to a conduit, such as a duct 12, or the like. A leveling device 150 is positioned on the mounting ring 138 and preferably the exterior surface of the flange 142. The leveling device 150 is preferably a bubble level that allows a user to determine whether the mounting ring 138 is level when mounting to a duct 12. At least one retention rib 124' is positioned on the mounting ring 138. Preferably at least two or more retention ribs 124' are positioned on the mounting ring 138 and spaced-apart from each other, and more preferably and as illustrated, a plurality of retention ribs 124' are positioned on the mounting ring 138 and spaced-apart from each other, and as illustrated, four retention ribs 124' are positioned on the mounting ring 138 and spaced an equal distance apart from each other. The retention ribs 124' are disposed on the exterior surface of the inner ring 140 and proximate the exterior surface of the flange 142.

The retention ribs 124' contain an upper surface and a bottom surface, the initial portion of the upper surface may be inclined to facilitate rotational engagement of the ion generation device 80 with the mounting ring 138. While the initial portion of the upper surface of the retention rib 124' may be inclined, the remaining portion of the upper surface is generally flat or linear and configured to receive the engaging surface 130 of an engagement strut 120. The retention rib 124' may not have an inclined initial portion and maintain a generally constant width along the length of the retention rib 124'. Stop surfaces 134' are disposed on the distal end of the retention rib 124' that limits rotational movement of the ion generation device 80 within the passageway 144 of the mounting ring 138. A tab 136' is disposed proximate the retention rib 124' and spaced-apart from the stop surface 134' of the retention rib 124' and perpendicular to the upper surface retention rib 124'.

During engagement of the ion generation device 80 to the adaptor 10, the top portion 98 of the ion generation device 80 is received within the passageway 144 of the mounting ring 138 until the outer edge of the inner ring 140 contacts the engagement member 90 of the ion generation device 80. The ion generation device 80 is rotated, preferably clockwise, causing the engaging surface 130 to contact the upper surface of the retention rib 124' and slide along the upper surface of the retention rib 124'. As the engaging surface 130 proceeds along the upper surface of the retention rib 124', the engaging surface 130 also slides along the exterior surface of the tab 136' and the cam surface 132 slides along the upper surface of the retention rib 124' and exterior surface of the tab 136'. Once the downside or declining portion of the cam surface 132 progresses past the tab 136', the tab 136' resists movement in the counter-clockwise direction because of a slight point or edge within on the cam surface 132 engages the tab 136' and the tab 136' prevents further movement in the counter-clockwise direction. As the ion generation device 10 is rotated, the shoulder portion 126 engages the stop surface 134', preventing further movement in the clockwise direction of the ion generation device 80.

The mounting ring 138 is preferably utilized with a duct 12 that has a flat surface. The process of mounting involves drilling a hole into a duct 12, wherein the hole drilled has a diameter slightly larger than the diameter of the inner ring 140 of the mounting ring 138. Inserting a portion of the mounting ring 138 into the hole in the duct 12 and placing the interior surface of the flange 142 adjacent the exterior surface of the duct 12. Ensuring the mounting ring 138 is level with respect to the exterior surface of the duct 12 by utilizing the leveling device 150. After the leveling device 150 indicates the mounting ring 138 is level, attaching the mounting ring 138 to the duct 12 by inserting engagement devices, such as a screw into each mounting bore 146 and screwing the screw into the duct 12. In this arrangement, a portion of the exterior surface of the inner ring 140 of the mounting ring 138 surrounds the exterior portion of the hole in the duct 12 and a portion of the inner ring 140 extends outwardly from the hole in the duct 12 and above the exterior surface of the flange 142. A portion of the ion generation device 80 is inserted into the passageway 144, and preferably the top portion 98 of the ion generation device 80 is inserted into the passageway 144 such that the electrodes 114 are positioned within the interior portion of the duct 12 for emitting ions within the flow of air through the duct 12. The ion generation device 80 is engaged to the mounting ring 138 as described herein.

During use, once power is provided to the control module 108 of the device 10, the device 10 initiates an internal check on all systems. After initializing and the check has confirmed all systems are operational, the light contained within a light aperture within the base portion 84 will blink "on" indicating power has been supplied to the device 10 and the device 10 is in the "on" position. The light is preferably a light-emitting diode with power supplied by the control module 108 and controlled by the control module 108. The cleaning cycle, whereby the cleaning device 106 rotates, thus contacting each electrode 114, is controlled by the control module 108. The control module 108 contains the logic for initiating and controlling the cleaning cycle, whereby power is supplied to the motor 104, causing the rotational shaft of the motor 104 to rotate, thus rotating the cleaning device 106. The logic controls the operation of the motor (the speed, time intervals, and length of time the rotational shaft of the motor 104 rotates) and thus controls the operation of the cleaning device 106, such as speed the cleaning device 106 rotates, the time intervals for rotating the cleaning device 106, and the length of time the cleaning device 106 rotates.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. An adaptor configured to adapt to a surface of a duct, the adapter comprising:
   a back portion with an aperture disposed within the back portion;
   a bellow adjacent the back portion with an opening corresponding to the aperture in the back portion; and
   a ring member disposed within the aperture and engaged to the bellow, wherein the ring member is configured to receive an ion generation device, and wherein upon placement of the ion generation device, the ion generation device is positioned at least partially within the aperture disposed within the back portion, wherein the adapter is held into place relative to the duct via at least one elongate retention device defined around the duct.

2. The adaptor according to claim 1, further comprising a top portion with a central opening configured to allow the bellow and ring member to extend there through.

3. The adaptor according to claim 1, wherein the bellow is flexible.

4. The adaptor according to claim 1, wherein the back portion contains a plurality of slots surrounding the aperture.

5. The adaptor according to claim 1, wherein the ring member is pivotally connected to the back portion.

6. The adaptor according to claim 1, further comprising a top portion adjacent an engagement surface of the bellow disposed along the periphery of the bellow, wherein a portion of the bellow and ring member extend through a central opening in the top portion.

7. An adaptor, comprising:
   a back portion containing an aperture that extends from the front side to the back side of the back portion;
   a bellow adjacent the front side of the back portion containing an opening; and
   a ring member disposed within the aperture of the back portion and the opening of the bellow containing an interior surface and an exterior surface, wherein the interior surface defines a passageway and the exterior surface is engaged to the bellow, wherein the ring member is configured to receive an ion generation device, and wherein upon placement of the ion generation device, the ion generation device is positioned at least partially within the aperture disposed within the back portion, wherein the adapter is held into place relative to a duct via at least one elongate retention device defined around the duct.

8. The adaptor according to claim 7, further comprising a top portion adjacent spaced-apart from the back portion by the bellow and including at least one bracket for receiving an elongate retention device for engaging the adaptor to the surface of a duct.

9. The adaptor according to claim 7, further comprising a retention rib for engaging an ion generation device.

10. The adaptor according to claim 7, wherein the ring member is rotationally engaged to the back portion.

11. An ion generation device, comprising:
   a base portion with a circular cross-section;
   an engagement member disposed within a cavity of the base portion;

a top portion adjacent the engagement member;

an ionization module electrically coupled to at least one electrode disposed adjacent the exterior surface of the top portion for emitting ions into the air surrounding the ion generation device; and a cleaning device for contacting the electrodes, wherein the cleaning device is a t-shape with a crossbar of the t-shape extending in two directions to contact the electrodes, wherein the crossbar is curved in a direction of the top portion to contact the electrodes.

12. The ion generation device according to claim 11, further comprising an electrode retention clip disposed within an electrode bore positioned on the top portion, wherein the electrode retention clip contains a top portion and a hollow shaft, whereby the hollow shaft is inserted into the electrode bore and configured for the electrode to be at least partially contained within the hollow shaft and a portion of the electrode extending through a bore in the top portion of the ion generation device.

13. The ion generation device of claim 11, wherein at least a portion of the base portion is removable from the engagement member to allow for securing of the ion generation device.

14. The ion generation device of claim 11, wherein the at least one electrode of the ionization module comprises a first electrode and a second electrode, wherein the cleaning device contacts each of the first electrode and the second electrode during a cleaning process.

15. The ion generation device of claim 14, wherein the first electrode and the second electrode are spaced at 180 degrees from one another.

16. The ion generation device of claim 14, wherein the cleaning device comprises a t-shape that extends outwardly, wherein the cleaning device contacts the first electrode and the second electrode simultaneously during the cleaning process.

17. The ion generation device of claim 14, wherein the cleaning device defines a bar that rotates about a center of the top portion.

18. The ion generation device of claim 17, wherein the bar is fixed in a curved position in the direction of the top portion.

19. The ion generation device of claim 11, further comprising an adapter configured to adapt to a surface of a duct, wherein the adapter comprises a back portion with an aperture disposed within the back portion, a bellow adjacent the back portion with an opening corresponding to the aperture in the back portion; and a ring member disposed within the aperture and engaged to the bellow, wherein the ring member is configured to engage the engagement member, and wherein upon engagement between the ring member and the engagement member, the top portion is positioned at least partially within the aperture disposed within the back portion, wherein the adapter is held into place relative to a duct via at least one elongate retention device defined around the duct.

20. The ion generation device of claim 19, wherein the adapter is attachable to a circular duct.

* * * * *